United States Patent
Wu et al.

(10) Patent No.: US 9,150,655 B2
(45) Date of Patent: Oct. 6, 2015

(54) ANTI-C-MET ANTIBODY AND METHODS OF USE THEREOF

(75) Inventors: Han-Chung Wu, Taipei (TW); Ruei-Min Lu, Sanchong (TW)

(73) Assignees: ACADEMIA SINICA, Nankang, Taipei (TW); Chi-Ming Liang, Bethesda, MD (US)

( * ) Notice: Subject to any disclaimer, the term of this patent is extended or adjusted under 35 U.S.C. 154(b) by 177 days.

(21) Appl. No.: 13/818,283

(22) PCT Filed: Aug. 30, 2011

(86) PCT No.: PCT/US2011/049763
§ 371 (c)(1),
(2), (4) Date: Apr. 29, 2013

(87) PCT Pub. No.: WO2012/030842
PCT Pub. Date: Mar. 8, 2012

(65) Prior Publication Data
US 2013/0209365 A1 Aug. 15, 2013

Related U.S. Application Data

(60) Provisional application No. 61/402,788, filed on Sep. 3, 2010.

(51) Int. Cl.
| | | |
|---|---|---|
| C07K 16/28 | (2006.01) | |
| A61K 9/127 | (2006.01) | |
| A61K 47/48 | (2006.01) | |
| A61K 49/00 | (2006.01) | |
| A61K 9/00 | (2006.01) | |
| A61K 47/24 | (2006.01) | |
| A61K 39/00 | (2006.01) | |

(52) U.S. Cl.
CPC ........... *C07K 16/2869* (2013.01); *A61K 9/0019* (2013.01); *A61K 9/1271* (2013.01); *A61K 47/24* (2013.01); *A61K 47/48823* (2013.01); *A61K 49/0058* (2013.01); *A61K 49/0067* (2013.01); *C07K 16/2863* (2013.01); *A61K 2039/505* (2013.01); *C07K 2317/622* (2013.01); *C07K 2317/77* (2013.01); *C07K 2317/92* (2013.01); *C07K 2319/30* (2013.01)

(58) Field of Classification Search
CPC ........... C07K 16/2863; C07K 16/2869; C07K 16/464; C07K 2317/24
See application file for complete search history.

(56) References Cited

U.S. PATENT DOCUMENTS

| 2010/0129369 A1 | 5/2010 | Davies et al. |
| 2010/0254988 A1 | 10/2010 | Bossenmaier et al. |

FOREIGN PATENT DOCUMENTS

| CA | 2694418 | | 1/2009 |
|---|---|---|---|
| EP | 2014681 | | 1/2009 |
| WO | 9738731 | A1 | 10/1997 |
| WO | 2004072117 | | 8/2004 |
| WO | WO2006/015371 | A2 * | 2/2006 |
| WO | WO2007/090807 | A1 * | 8/2007 |
| WO | 2007/126799 | | 11/2007 |
| WO | WO2007/126799 | A2 * | 11/2007 |
| WO | 2009007427 | A2 | 1/2009 |
| WO | 2010045344 | A1 | 4/2010 |
| WO | 2010059654 | | 5/2010 |
| WO | 2010/069765 | | 6/2010 |
| WO | 2010064089 | | 10/2010 |
| WO | 2011/150454 | | 12/2011 |

OTHER PUBLICATIONS

Maulik et al., Cytokine & Growth Factor Rev. 2002; 13:41-59.*
Almagro & Fransson, Frontiers in Bioscience 2008; 13:1619-33.*
De Genst et al., Dev Comp Immunol 2006; 30:187-98.*
PJ Carter, Nat Rev Immunol, 2006; 6:343-357.*
GenBank Accession No. NP_000236.2 "hepatocyte growth factor receptor isoform b precursor [*Homo sapiens*]" downloaded Dec. 23, 2013 from //www.ncbi.nlm.nih.gov/protein/42741655.
Cheng et al., "The use of single chain Fv as targeting agents for immunoliposomes: an update on immunoliposomal drugs for cancer treatment", Expert Opin Drug Deliv (Apr. 2010), 7(4):461-478.
Van Der Horst Eh et al., "Discovery of fully human anti-MET monoclonal antibodies with antitumor activity against colon cancer tumor models in vivo", Neoplasia (Apr. 2009), 11(4):355-364.
ElBayoumi; et al., "Tumor-targeted nanomedicines: enhanced antitumor efficacy in vivo of doxorubicin-loaded, long-circulating liposomes modified with cancer-specific monoclonal antibody", Clinical Cancer Research (Mar. 2009), 15 (6):1973-80.
Jin; et al., "MetMAb, the one-armed 5D5 anti-c-Met antibody, inhibits orthotopic pancreatic tumor growth and improves survival", Cancer Research (Jun. 2008), 68(11):4360-8.

* cited by examiner

*Primary Examiner* — Sheela J Huff
*Assistant Examiner* — Jessica H Roark
(74) *Attorney, Agent, or Firm* — Bozicevic, Field & Francis LLP; Pamela J. Sherwood

(57) ABSTRACT

Antibodies that bind to c-Met are provided herein, as well as related compositions and methods of use. Methods of use encompass cancer therapies and diagnostics. In certain embodiments, antibodies bind mammalian cell surface antigen (e.g., cancer cell surface antigen). The antibodies can also be endocytosed upon binding to cells. Cells that can be targeted by the antibodies include carcinomas, such as those in lung, kidney, liver, stomach, breast, and brain, etc.

16 Claims, 14 Drawing Sheets

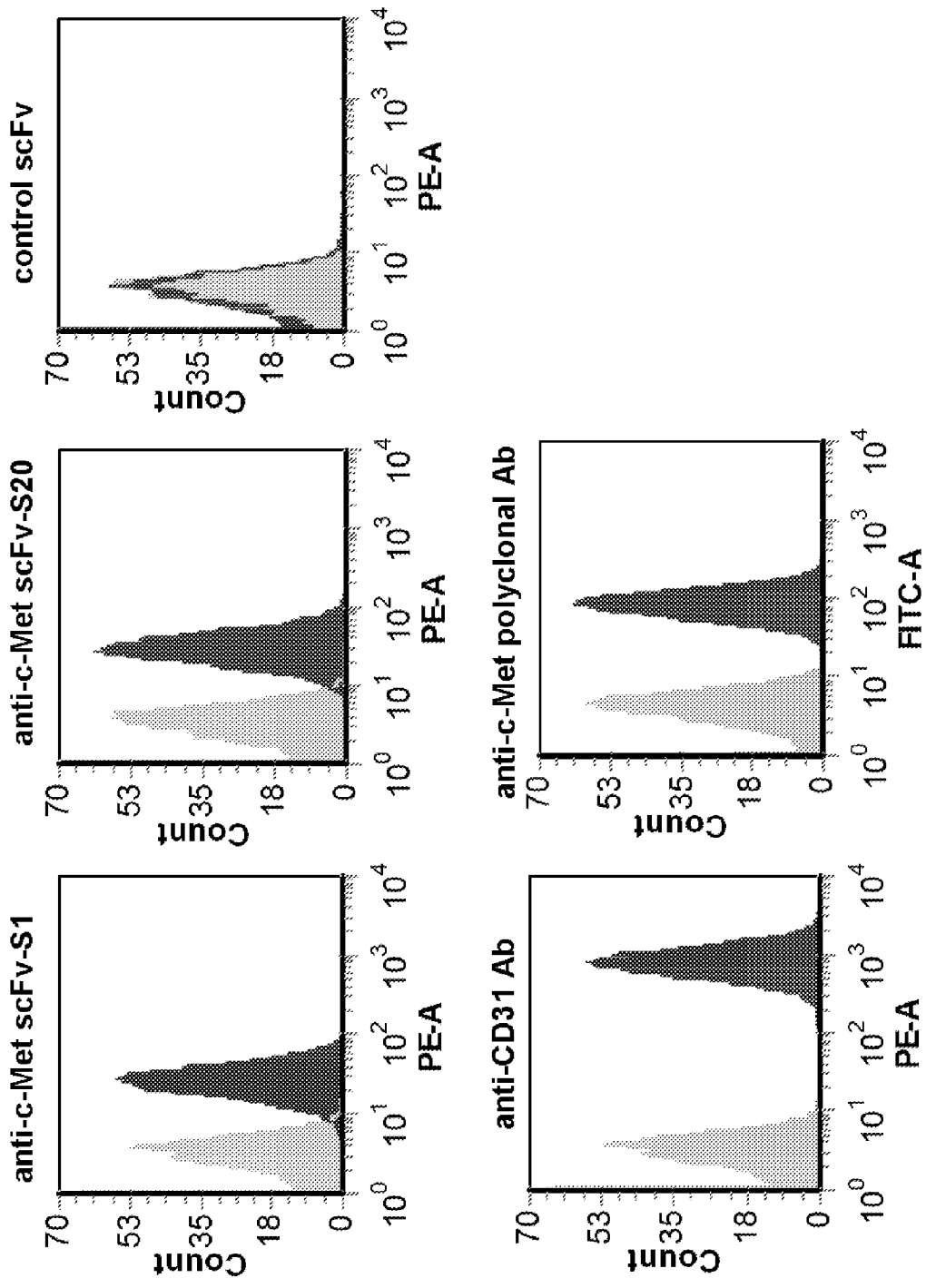

SEQUENCE LISTING

```
<160> NUMBER OF SEQ ID NOS: 50

<210> SEQ ID NO 1
<211> LENGTH: 5
<212> TYPE: PRT
<213> ORGANISM: Artificial Sequence
<220> FEATURE:
<223> OTHER INFORMATION: Synthetic peptide

<400> SEQUENCE: 1

Gly Ser Gly Gly Ser
1               5

<210> SEQ ID NO 2
<211> LENGTH: 4
<212> TYPE: PRT
<213> ORGANISM: Artificial Sequence
<220> FEATURE:
<223> OTHER INFORMATION: Synthetic peptide

<400> SEQUENCE: 2

Gly Gly Gly Ser
1

<210> SEQ ID NO 3
<211> LENGTH: 4
<212> TYPE: PRT
<213> ORGANISM: Artificial Sequence
<220> FEATURE:
```

```
<223> OTHER INFORMATION: Synthetic peptide

<400> SEQUENCE: 3

Gly Gly Ser Gly
  1

<210> SEQ ID NO 4
<211> LENGTH: 5
<212> TYPE: PRT
<213> ORGANISM: Artificial Sequence
<220> FEATURE:
<223> OTHER INFORMATION: Synthetic peptide

<400> SEQUENCE: 4

Gly Gly Ser Gly Gly
  1               5

<210> SEQ ID NO 5
<211> LENGTH: 5
<212> TYPE: PRT
<213> ORGANISM: Artificial Sequence
<220> FEATURE:
<223> OTHER INFORMATION: Synthetic peptide

<400> SEQUENCE: 5

Gly Ser Gly Ser Gly
  1               5

<210> SEQ ID NO 6
<211> LENGTH: 5
<212> TYPE: PRT
<213> ORGANISM: Artificial Sequence
<220> FEATURE:
<223> OTHER INFORMATION: Synthetic peptide

<400> SEQUENCE: 6

Gly Ser Gly Gly Gly
  1               5

<210> SEQ ID NO 7
<211> LENGTH: 5
<212> TYPE: PRT
<213> ORGANISM: Artificial Sequence
<220> FEATURE:
<223> OTHER INFORMATION: Synthetic peptide

<400> SEQUENCE: 7

Gly Gly Gly Ser Gly
  1               5

<210> SEQ ID NO 8
<211> LENGTH: 5
<212> TYPE: PRT
<213> ORGANISM: Artificial Sequence
<220> FEATURE:
<223> OTHER INFORMATION: Synthetic peptide

<400> SEQUENCE: 8

Gly Ser Ser Ser Gly
  1               5

<210> SEQ ID NO 9
<211> LENGTH: 30
<212> TYPE: PRT
<213> ORGANISM: Artificial Sequence
<220> FEATURE:
<223> OTHER INFORMATION: Synthetic peptide
```

<400> SEQUENCE: 9

Met Ala Gln Val Gln Leu Gln Gln Ser Gly Pro Gly Leu Val Lys Pro
1               5                   10                  15

Ser Gln Thr Leu Ser Leu Thr Cys Asp Ile Ser Gly Asp Ser
            20                  25                  30

<210> SEQ ID NO 10
<211> LENGTH: 8
<212> TYPE: PRT
<213> ORGANISM: Artificial Sequence
<220> FEATURE:
<223> OTHER INFORMATION: Synthetic peptide

<400> SEQUENCE: 10

Val Ser Ser Asn Ser Ala Ala Trp
1               5

<210> SEQ ID NO 11
<211> LENGTH: 14
<212> TYPE: PRT
<213> ORGANISM: Artificial Sequence
<220> FEATURE:
<223> OTHER INFORMATION: Synthetic peptide

<400> SEQUENCE: 11

Asn Trp Ile Arg Gln Ser Pro Ser Arg Gly Leu Glu Trp Leu
1               5                   10

<210> SEQ ID NO 12
<211> LENGTH: 19
<212> TYPE: PRT
<213> ORGANISM: Artificial Sequence
<220> FEATURE:
<223> OTHER INFORMATION: Synthetic peptide

<400> SEQUENCE: 12

Gly Arg Thr Tyr Tyr Arg Ser Arg Trp Tyr Asn Glu Tyr Ala Val Ser
1               5                   10                  15

Val Arg Gly

<210> SEQ ID NO 13
<211> LENGTH: 30
<212> TYPE: PRT
<213> ORGANISM: Artificial Sequence
<220> FEATURE:
<223> OTHER INFORMATION: Synthetic peptide

<400> SEQUENCE: 13

Met Ala Gln Val Gln Leu Gln Gln Ser Gly Gly Lys Leu Val Gln Pro
1               5                   10                  15

Arg Gly Ser Leu Arg Leu Ser Cys Ala Ala Ser Gly Phe Ser
            20                  25                  30

<210> SEQ ID NO 14
<211> LENGTH: 6
<212> TYPE: PRT
<213> ORGANISM: Artificial Sequence
<220> FEATURE:
<223> OTHER INFORMATION: Synthetic peptide

<400> SEQUENCE: 14

Leu Gly Ser Tyr Ala Met
1               5

<210> SEQ ID NO 15
<211> LENGTH: 14
<212> TYPE: PRT
<213> ORGANISM: Artificial Sequence
<220> FEATURE:
<223> OTHER INFORMATION: Synthetic peptide

<400> SEQUENCE: 15

Ser Trp Val Arg Gln Ala Pro Gly Lys Gly Leu Glu Trp Val
1               5                   10

<210> SEQ ID NO 16
<211> LENGTH: 17
<212> TYPE: PRT
<213> ORGANISM: Artificial Sequence
<220> FEATURE:
<223> OTHER INFORMATION: Synthetic peptide

<400> SEQUENCE: 16

Ser Thr Lys Asp Ser Asp Gly Thr Thr Tyr Tyr Ala Asp Ser Val Arg
1               5                   10                  15

Gly

<210> SEQ ID NO 17
<211> LENGTH: 30
<212> TYPE: PRT
<213> ORGANISM: Artificial Sequence
<220> FEATURE:
<223> OTHER INFORMATION: Synthetic peptide

<400> SEQUENCE: 17

Met Ala Glu Val Gln Leu Val Glu Ser Gly Pro Gly Leu Val Lys Pro
1               5                   10                  15
Ser Gly Thr Leu Ser Leu Lys Cys Asp Ala Ser Ala Ile Ser
            20                  25                  30

<210> SEQ ID NO 18
<211> LENGTH: 7
<212> TYPE: PRT
<213> ORGANISM: Artificial Sequence
<220> FEATURE:
<223> OTHER INFORMATION: Synthetic peptide

<400> SEQUENCE: 18

Met Asp Ser Asn Tyr Trp Trp
1               5

<210> SEQ ID NO 19
<211> LENGTH: 14
<212> TYPE: PRT
<213> ORGANISM: Artificial Sequence
<220> FEATURE:
<223> OTHER INFORMATION: Synthetic peptide

<400> SEQUENCE: 19

Ser Trp Leu Arg Gln Pro Pro Gly Lys Gly Leu Glu Trp Ile
1               5                   10

<210> SEQ ID NO 20
<211> LENGTH: 17
<212> TYPE: PRT
<213> ORGANISM: Artificial Sequence
<220> FEATURE:
<223> OTHER INFORMATION: Synthetic peptide

<400> SEQUENCE: 20

```
Gly Glu Ile Ser His Ser Gly Ser Thr Asp Tyr Asn Pro Ser Leu Lys
 1               5                  10                  15

Ser
```

<210> SEQ ID NO 21
<211> LENGTH: 32
<212> TYPE: PRT
<213> ORGANISM: Artificial Sequence
<220> FEATURE:
<223> OTHER INFORMATION: Synthetic peptide

<400> SEQUENCE: 21

```
Arg Ile Ser Ile Asn Ala Glu Thr Ser Lys Asn Gln Phe Ser Leu Gln
 1               5                  10                  15

Leu Asn Ser Val Thr Pro Glu Asp Thr Ala Ile Tyr Tyr Cys Ala Arg
            20                  25                  30
```

<210> SEQ ID NO 22
<211> LENGTH: 15
<212> TYPE: PRT
<213> ORGANISM: Artificial Sequence
<220> FEATURE:
<223> OTHER INFORMATION: Synthetic peptide

<400> SEQUENCE: 22

```
Ala Gly Phe Cys Ser Gly Gly Asn Cys Tyr Pro Gly Ser Glu Asp
 1               5                  10                  15
```

<210> SEQ ID NO 23
<211> LENGTH: 13
<212> TYPE: PRT
<213> ORGANISM: Artificial Sequence
<220> FEATURE:
<223> OTHER INFORMATION: Synthetic peptide

<400> SEQUENCE: 23

```
Ala Phe Asp Leu Trp Gly Gln Gly Thr Met Val Thr Val
 1               5                  10
```

<210> SEQ ID NO 24
<211> LENGTH: 32
<212> TYPE: PRT
<213> ORGANISM: Artificial Sequence
<220> FEATURE:
<223> OTHER INFORMATION: Synthetic peptide

<400> SEQUENCE: 24

```
Arg Phe Thr Ile Ala Arg Asp Asn Ser Lys Asn Thr Leu Tyr Leu Gln
 1               5                  10                  15

Met Asn Ser Leu Arg Ala Glu Asp Thr Ala Ile Tyr Tyr Cys Ala Arg
            20                  25                  30
```

<210> SEQ ID NO 25
<211> LENGTH: 7
<212> TYPE: PRT
<213> ORGANISM: Artificial Sequence
<220> FEATURE:
<223> OTHER INFORMATION: Synthetic peptide

<400> SEQUENCE: 25

```
Asp Phe Pro Gly Gly Pro Asn
 1               5
```

<210> SEQ ID NO 26

```
<211> LENGTH: 13
<212> TYPE: PRT
<213> ORGANISM: Artificial Sequence
<220> FEATURE:
<223> OTHER INFORMATION: Synthetic peptide

<400> SEQUENCE: 26

Ala Phe Asp Phe Trp Gly Gln Gly Thr Met Val Thr Val
 1               5                  10

<210> SEQ ID NO 27
<211> LENGTH: 31
<212> TYPE: PRT
<213> ORGANISM: Artificial Sequence
<220> FEATURE:
<223> OTHER INFORMATION: Synthetic peptide

<400> SEQUENCE: 27

Arg Ala Thr Ile Ser Ile Asp Lys Ser Lys Lys Gln Phe Phe Leu Arg
 1               5                  10                  15

Leu Lys Ser Val Thr Ala Ala Asp Thr Ala Val Tyr Tyr Cys Ala
            20                  25                  30

<210> SEQ ID NO 28
<211> LENGTH: 7
<212> TYPE: PRT
<213> ORGANISM: Artificial Sequence
<220> FEATURE:
<223> OTHER INFORMATION: Synthetic peptide

<400> SEQUENCE: 28

Gly Leu Leu Ser Pro Leu Asp
 1               5

<210> SEQ ID NO 29
<211> LENGTH: 13
<212> TYPE: PRT
<213> ORGANISM: Artificial Sequence
<220> FEATURE:
<223> OTHER INFORMATION: Synthetic peptide

<400> SEQUENCE: 29

Ala Phe Asp Glu Trp Gly Gln Gly Thr Met Val Thr Val
 1               5                  10

<210> SEQ ID NO 30
<211> LENGTH: 22
<212> TYPE: PRT
<213> ORGANISM: Artificial Sequence
<220> FEATURE:
<223> OTHER INFORMATION: Synthetic peptide

<400> SEQUENCE: 30

Asp Val Val Met Thr Gln Ser Pro Pro Ser Leu Ser Val Ser Val Gly
 1               5                  10                  15

Asp Arg Val Thr Ile Thr
            20

<210> SEQ ID NO 31
<211> LENGTH: 12
<212> TYPE: PRT
<213> ORGANISM: Artificial Sequence
<220> FEATURE:
<223> OTHER INFORMATION: Synthetic peptide

<400> SEQUENCE: 31
```

Cys Arg Ala Ser Gln Asp Ile Thr Asn Asp Leu Asn
1               5                   10

<210> SEQ ID NO 32
<211> LENGTH: 15
<212> TYPE: PRT
<213> ORGANISM: Artificial Sequence
<220> FEATURE:
<223> OTHER INFORMATION: Synthetic peptide

<400> SEQUENCE: 32

Trp Tyr Gln Gln Lys Pro Gly Lys Ala Pro Gln Leu Leu Ile Tyr
1               5                   10                  15

<210> SEQ ID NO 33
<211> LENGTH: 7
<212> TYPE: PRT
<213> ORGANISM: Artificial Sequence
<220> FEATURE:
<223> OTHER INFORMATION: Synthetic peptide

<400> SEQUENCE: 33

His Ala Ser Glu Leu Glu Thr
1               5

<210> SEQ ID NO 34
<211> LENGTH: 22
<212> TYPE: PRT
<213> ORGANISM: Artificial Sequence
<220> FEATURE:
<223> OTHER INFORMATION: Synthetic peptide

<400> SEQUENCE: 34

Asp Ile Val Met Thr Gln Ser Pro Ala Thr Leu Ser Leu Ser Pro Gly
1               5                   10                  15

Glu Arg Ala Thr Leu Ser
            20

<210> SEQ ID NO 35
<211> LENGTH: 12
<212> TYPE: PRT
<213> ORGANISM: Artificial Sequence
<220> FEATURE:
<223> OTHER INFORMATION: Synthetic peptide

<400> SEQUENCE: 35

Cys Arg Ala Ser Gln Ser Ile Thr Thr Tyr Leu Val
1               5                   10

<210> SEQ ID NO 36
<211> LENGTH: 15
<212> TYPE: PRT
<213> ORGANISM: Artificial Sequence
<220> FEATURE:
<223> OTHER INFORMATION: Synthetic peptide

<400> SEQUENCE: 36

Trp Tyr Gln Gln Lys Pro Gly Gln Ala Pro Arg Leu Leu Ile Tyr
1               5                   10                  15

<210> SEQ ID NO 37
<211> LENGTH: 7
<212> TYPE: PRT
<213> ORGANISM: Artificial Sequence
<220> FEATURE:
<223> OTHER INFORMATION: Synthetic peptide

```
<400> SEQUENCE: 37

Asp Ala Ser Asn Arg Ala Thr
1               5

<210> SEQ ID NO 38
<211> LENGTH: 22
<212> TYPE: PRT
<213> ORGANISM: Artificial Sequence
<220> FEATURE:
<223> OTHER INFORMATION: Synthetic peptide

<400> SEQUENCE: 38

Asp Ile Gln Met Thr Gln Ser Pro Ser Ser Leu Ser Ala Ser Val Gly
1               5                   10                  15

Asp Arg Val Thr Ile Thr
            20

<210> SEQ ID NO 39
<211> LENGTH: 12
<212> TYPE: PRT
<213> ORGANISM: Artificial Sequence
<220> FEATURE:
<223> OTHER INFORMATION: Synthetic peptide

<400> SEQUENCE: 39

Cys Arg Ala Ser Gln Arg Val Ala Thr Tyr Leu Asn
1               5                   10

<210> SEQ ID NO 40
<211> LENGTH: 15
<212> TYPE: PRT
<213> ORGANISM: Artificial Sequence
<220> FEATURE:
<223> OTHER INFORMATION: Synthetic peptide

<400> SEQUENCE: 40

Trp Tyr Gln Gln Lys Pro Gly Lys Ala Pro Asn Leu Leu Ile Tyr
1               5                   10                  15

<210> SEQ ID NO 41
<211> LENGTH: 7
<212> TYPE: PRT
<213> ORGANISM: Artificial Sequence
<220> FEATURE:
<223> OTHER INFORMATION: Synthetic peptide

<400> SEQUENCE: 41

Glu Ala Ser Ser Leu Gln Ser
1               5

<210> SEQ ID NO 42
<211> LENGTH: 32
<212> TYPE: PRT
<213> ORGANISM: Artificial Sequence
<220> FEATURE:
<223> OTHER INFORMATION: Synthetic peptide

<400> SEQUENCE: 42

Gly Val Pro Ser Arg Phe Ser Gly Ser Gly Phe Gly Thr Asp Phe Thr
1               5                   10                  15
```

```
Leu Thr Ile Ser Ser Leu Gln Pro Ala Asp Ile Ala Thr Tyr Tyr Cys
            20                  25                  30

<210> SEQ ID NO 43
<211> LENGTH: 9
<212> TYPE: PRT
<213> ORGANISM: Artificial Sequence
<220> FEATURE:
<223> OTHER INFORMATION: Synthetic peptide

<400> SEQUENCE: 43

Gln Gln Tyr Asp Asp Leu Pro Leu Thr
1               5

<210> SEQ ID NO 44
<211> LENGTH: 11
<212> TYPE: PRT
<213> ORGANISM: Artificial Sequence
<220> FEATURE:
<223> OTHER INFORMATION: Synthetic peptide

<400> SEQUENCE: 44

Phe Gly Gly Gly Thr Lys Val Glu Ile Lys Arg
1               5                  10

<210> SEQ ID NO 45
<211> LENGTH: 32
<212> TYPE: PRT
<213> ORGANISM: Artificial Sequence
<220> FEATURE:
<223> OTHER INFORMATION: Synthetic peptide

<400> SEQUENCE: 45

Gly Ile Pro Ala Arg Phe Ser Gly Ser Gly Ser Gly Thr Asp Phe Thr
1               5                   10                  15

Leu Thr Ile Ser Ser Leu Glu Pro Glu Asp Phe Ala Val Tyr Phe Cys
            20                  25                  30

<210> SEQ ID NO 46
<211> LENGTH: 9
<212> TYPE: PRT
<213> ORGANISM: Artificial Sequence
<220> FEATURE:
<223> OTHER INFORMATION: Synthetic peptide

<400> SEQUENCE: 46

Gln Gln Arg Ser Asp Trp Pro Pro Thr
1               5

<210> SEQ ID NO 47
<211> LENGTH: 11
<212> TYPE: PRT
<213> ORGANISM: Artificial Sequence
<220> FEATURE:
<223> OTHER INFORMATION: Synthetic peptide

<400> SEQUENCE: 47

Phe Gly Gly Gly Thr Lys Val Glu Ile Lys Arg
1               5                  10

<210> SEQ ID NO 48
<211> LENGTH: 32
<212> TYPE: PRT
<213> ORGANISM: Artificial Sequence
<220> FEATURE:
<223> OTHER INFORMATION: Synthetic peptide
```

```
-continued

<400> SEQUENCE: 48

Gly Val Pro Ser Arg Phe Ser Gly Arg Arg Ser Gly Thr Asp Phe Thr
1               5                   10                  15

Leu Thr Ile Ser Ser Leu Gln Pro Glu Asp Phe Ala Thr Tyr Tyr Cys
                20                  25                  30

<210> SEQ ID NO 49
<211> LENGTH: 9
<212> TYPE: PRT
<213> ORGANISM: Artificial Sequence
<220> FEATURE:
<223> OTHER INFORMATION: Synthetic peptide

<400> SEQUENCE: 49

Gln Gln Ser Tyr Asn Thr Pro Tyr Thr
1               5

<210> SEQ ID NO 50
<211> LENGTH: 11
<212> TYPE: PRT
<213> ORGANISM: Artificial Sequence
<220> FEATURE:
<223> OTHER INFORMATION: Synthetic peptide

<400> SEQUENCE: 50

Phe Gly Gln Gly Thr Arg Leu Glu Ile Lys Arg
1               5                   10
```

ANTI-C-MET ANTIBODY AND METHODS OF USE THEREOF

INTRODUCTION

Lung cancer is the leading cause of cancer-related death among men and women in the United States. Around 219,000 new lung cancer cases were diagnosed and 160,000 deaths due to this disease were estimated to have occurred in the U.S. in 2009. There are two well-known forms of lung cancer-small cell lung cancer (SCLC) and non-small cell lung cancer (NSCLC), the latter making up approximately 80% of lung cancers. The five-year survival rate for patients with NSCLC is about 16 percent. Although chemotherapy combined with surgical resection and radiotherapy have been applied to treatments for different stages of NSCLC, prognosis remains poor and recurrence runs as high as 10% following initial treatment.

c-Met, the receptor for hepatocyte growth factor, belongs to a subfamily of receptor tyrosine kinases (RTKs). In normal physiology, the HGF/c-Met pathway participates in various biological functions including cell proliferation, survival, motility, and wound healing (Birchmeier et al., 2003). However, aberrant c-Met activation, including gene amplification, mutation, and overexpression, has been reported in clinical cases with hematological malignancies and most solid tumors. c-Met activation has been reported to trigger cancer cell proliferation, migration and invasion, and promote tumor vessel angiogenesis because HGF directly stimulates endothelial cell proliferation and migration.

In addition, overexpressed c-Met has been frequently observed in patients with brain, colorectal, gastric, lung, head and neck and stomach cancer. The poor clinical outcomes were clearly correlated with elevated c-Met, suggesting that the overexpression of c-Met is a negative prognostic factor for tumor progression in these cancer types.

SUMMARY OF THE INVENTION

Antibodies that bind to c-Met, are disclosed herein, as well as related compositions and methods of use. Methods of use include, without limitation, cancer therapies and diagnostics. In certain embodiments, the antibodies of the invention bind mammalian cell surface antigen (e.g., cancer cell surface antigen). The antibodies can also be endocytosed upon binding to cells. Cells that can be targeted by the antibodies include carcinomas, such as those in lung, kidney, liver, stomach, breast, and brain, etc.

DEFINITIONS

Figure 1:
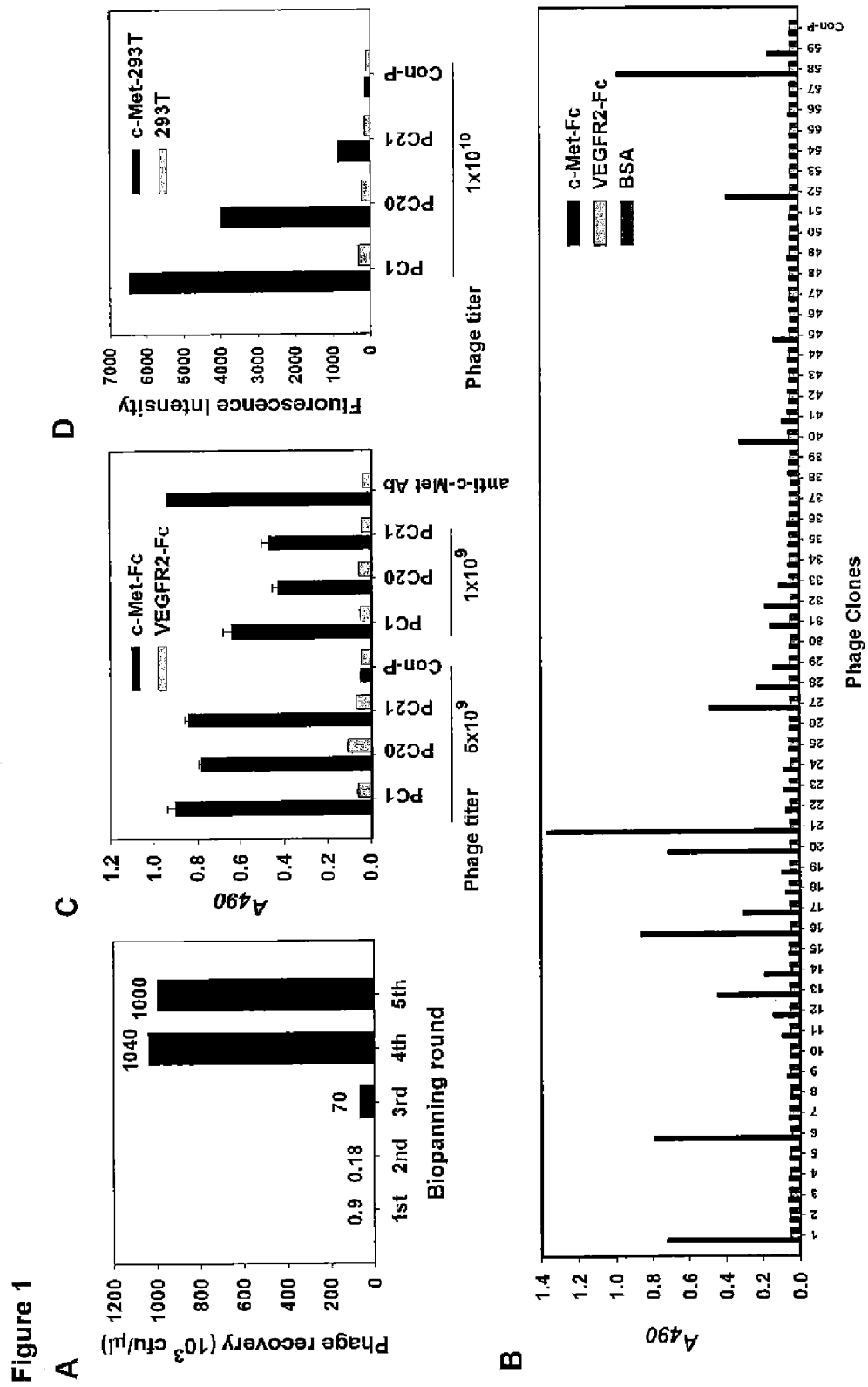
FIG. 1. Selection and identification of phage-displayed scFv that bound to c-Met protein. A, a phage-displayed human naïve scFv library was used to select phages that bound to c-Met-Fc protein (biopanning). B, the randomly selected phage clones were screened via ELISA to reveal different binding. C, comparison of the selected phage clones bound to c-Met-Fc protein with two different titers by ELISA. D, comparative cellular c-Met binding affinity of the phage clones were evaluated on c-Met-overexpressing 293T cells by flow cytometry. E, determination of the binding specificity of the phage clones by immunofluorescence staining. Scale bar: 50 μm.
Figure 1E:
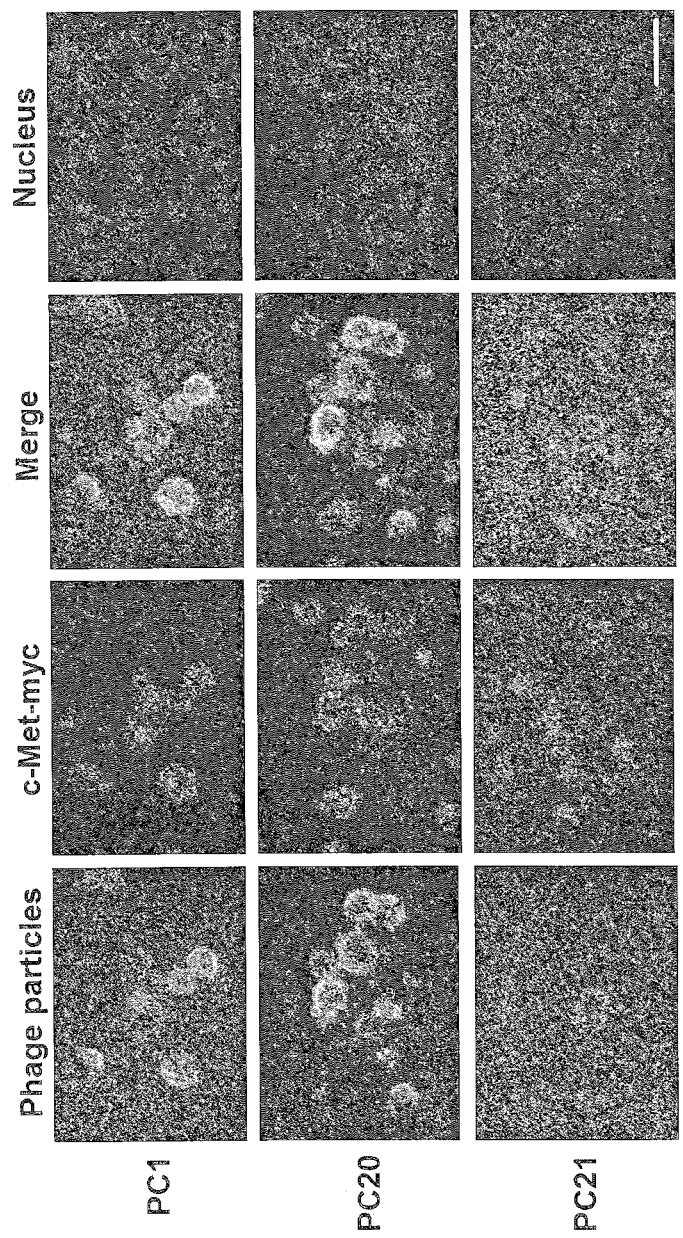

In the description that follows, a number of terms conventionally used in the field of cell culture are utilized extensively. In order to provide a clear and consistent understanding of the specification and claims, and the scope to be given to such terms, the following definitions are provided.

As used herein, "c-Met" refers to a member of receptor tyrosine kinase that can bind hepatocyte growth factor (HGF), and can also be named "hepatocyte growth factor receptor" (HGFR) or "met proto-oncogene". The term "c-Met" refers to any naturally-occurring isoforms of a c-Met protein. The amino acid sequences of c-Met are known and can be found as GenBank Accession Nos. NP_000236.2 and NP_001120972.1.

The terms "polypeptide", "peptide", or "protein" are used interchangeably herein to designate a linear series of amino acid residues connected one to the other by peptide bonds between the alpha-amino and carboxy groups of adjacent residues. In addition, the amino acids, in addition to the 20 "standard" genetically encodable amino acids, include amino acid analogs.

"Antibody" encompasses compositions comprising an antigen-binding protein, individually or as a preparation comprising a plurality thereof, having one or more polypeptides that can be genetically encodable by immunoglobulin genes, or fragments of immunoglobulin genes, or that comprise CDRs obtained or derived from a phage display library, and which bind an antigen of interest. Light chains are classified as either kappa or lambda. Heavy chains can be classified as gamma, mu, alpha, delta, or epsilon, which in turn define the immunoglobulin classes, IgG, IgM, IgA, IgD and IgE, respectively.

An example of an antibody is one having a structural unit of a tetramer composed of two pairs of polypeptide chains, each pair having one "light" and one "heavy" chain. The N-terminal portion of each chain defines a variable region that mediates antigen binding. The terms variable light chain ($V_L$) and variable heavy chain ($V_H$) refer to light and heavy chains respectively.

"Antibody" also encompasses single-chain antibodies that contain a heavy chain and a light chain linked together as a single polypeptide.

As noted above, "antibody" encompasses intact immunoglobulins as well antigen-binding fragments of antibodies. Thus, the term "antibody", as used herein also includes an antigen-binding portion of an antibody, which can be produced by the modification of whole antibodies or synthesized de novo using recombinant DNA methodologies. Examples include, but are not limited to, Fab', Fab'$_2$, or scFv.

A single chain Fv ("scFv") polypeptide is a covalently linked $V_H$::$V_L$ heterodimer which may be expressed from a nucleic acid including $V_H$- and $V_L$-encoding sequences either joined directly or joined by a peptide-encoding linker. A number of structures are available for converting the light and heavy polypeptide chains from an antibody V region into a scFv molecule which will fold into a three dimensional structure substantially similar to the structure of an antigen-binding site. In addition to being diabodies, the scFvs can also be present as tribodies or tetrabodies.

It should be noted that while various antibody fragments are defined in terms of the digestion of an intact antibody, one of skill will appreciate that such fragments may be synthesized de novo either chemically or by utilizing recombinant DNA methodology.

The term "antibody" encompasses polyclonal and monoclonal antibodies, and further encompasses antibodies of any class (e.g., IgM, IgG, and subclasses thereof). "Antibody" also encompasses hybrid antibodies, heteroantibodies, chimeric antibodies, humanized antibodies, and functional fragments thereof which retain antigen binding. The antibodies may be conjugated to other moieties, and/or may be bound to a support (e.g., a solid support), such as a polystyrene plate or bead, test strip, and the like.

An immunoglobulin light or heavy chain variable region is composed of a "framework" region (FR) interrupted by three hypervariable regions, also called complementarity determining regions" or "CDRs". The extent of the framework region and CDRs can be defined based on databases known in the art. See, for example, V Base at www.vbase2.org. The sequences of the framework regions of different light or heavy chains are relatively conserved within a species. The framework region of an antibody, that is the combined framework regions of the constituent light and heavy chains, serves to position and align the CDRs. The CDRs are primarily responsible for binding to an epitope of an antigen. All CDRs and framework provided by the present disclosure are defined according to V Base, unless otherwise indicated.

An "anti-c-Met antibody" refers to an antibody that, specifically binds to c-Met, preferably with high affinity. A specific antibody for c-Met does not exhibit comparable binding to other antigens unrelated to c-Met relative to the binding of c-Met.

The term "high affinity" when used with respect to an antibody refers to an antibody that specifically binds to ("recognizes") its target(s) with an affinity ($K_D$) value less than or equal to $10^{-6}$ M, less than $10^{-7}$ M, less than $10^{-8}$ M. A lower $K_D$ value corresponds to a higher binding affinity (i.e., stronger binding) so that a $K_D$ value of $10^{-7}$ indicates a higher binding affinity than a $K_D$ value of $10^{-6}$.

An "antigen-binding site" or "binding portion" refers to a part of an antibody molecule (e.g. fragment of an immunoglobulin molecule or scFv) that participates in immunoreactive antigen binding. The antigen binding site is formed by amino acid residues of the N-terminal variable ("V") regions of the heavy ("H") and/or light ("L") chains. Three highly divergent stretches within the V regions of the heavy and light chains are referred to as "hypervariable regions" which are interposed between more conserved flanking stretches known as "framework regions" or "FRs". Thus, the term "FR" refers to amino acid sequences that are naturally found between and adjacent to hypervariable regions in immunoglobulins. In a tetrameric antibody molecule, the three hypervariable regions of a light chain and the three hypervariable regions of a heavy chain are disposed relative to each other in three dimensional space to form an antigen binding "surface". This surface mediates recognition and binding of the target antigen. The three hypervariable regions of each of the heavy and/or light chains are referred to as "complementarity determining regions" or "CDRs".

An "epitope" is a site on an antigen (e.g. a site on the c-Met Sema or PSI domain) to which an antibody binds. Epitopes can be formed both from contiguous amino acids or noncontiguous amino acids juxtaposed by folding (e.g., tertiary folding) of a protein.

A "S21 antibody" or "antibody from clone 21" refers to an antibody expressed by clone S21 or clone 21 or to an antibody synthesized in other manners, but having the same CDRs and optionally, the same framework regions as the antibody expressed by clone S21. Similarly, antibodies S1 (clone 1) and S20 (clone 20), and the like refer to antibodies expressed by the corresponding clone(s) and/or to antibodies synthesized in other manners, but having the same CDRs and optionally, the same framework regions as the referenced antibodies. The CDRs of these antibodies are shown in Table 1 below.

The terms "subject," "individual," and "patient" are used interchangeably herein to refer to a mammal being assessed for treatment and/or being treated. In an embodiment, the mammal is a human. The terms "subject," "individual," and "patient" thus encompass individuals having cancer (e.g., lung cancer, adenocarcinoma of the ovary or prostate, breast carcinoma, etc.) Subjects may be human, but also include other mammals, particularly those mammals useful as laboratory models for human disease, e.g. mouse, rat, etc.

As used herein, the terms "treatment," "treating," and the like, refer to administering an agent, or carrying out a procedure (e.g., radiation, a surgical procedure, etc.), for the purposes of obtaining an effect. The effect may be prophylactic in terms of completely or partially preventing a disease or symptom thereof and/or may be therapeutic in terms of effecting a partial or complete cure for a disease and/or symptoms of the disease. "Treatment," as used herein, covers any treatment of any proliferative growth in a mammal, particularly in a human, and includes: (a) preventing the disease or a symptom of a disease from occurring in a subject which may be predisposed to the disease but has not yet been diagnosed as having it (e.g., including diseases that may be associated with or caused by a primary disease; (b) inhibiting the disease, i.e., arresting its development; and (c) relieving the disease, i.e., causing regression of the disease. In tumor (e.g., cancer) treatment, a therapeutic agent may directly decrease the metastasis of tumor cells.

The term "cell culture" or "culture" means the maintenance of cells in an artificial, in vitro environment. It is to be understood, however, that the term "cell culture" is a generic term and may be used to encompass the cultivation not only of individual cells, but also of tissues or organs.

The term "tumor," as used herein, refers to all neoplastic cell growth and proliferation, whether malignant or benign, and all pre-cancerous and cancerous cells and tissues.

The terms "cancer," "neoplasm," and "tumor" are used interchangeably herein to refer to cells which exhibit autonomous, unregulated growth, such that they exhibit an aberrant growth phenotype characterized by a significant loss of control over cell proliferation. In general, cells of interest for detection, analysis, classification, or treatment in the present application include precancerous (e.g., benign), malignant, pre-metastatic, metastatic, and non-metastatic cells. Examples of cancer include but are not limited to, lung cancer, kidney cancer (e.g. renal cancer), gastric cancer, breast cancer, brain cancer, lung cancer, prostate cancer, hepatocellular cancer, pancreatic cancer, cervical cancer, ovarian cancer, liver cancer, bladder cancer, cancer of the urinary tract, thyroid cancer, carcinoma, melanoma, head and neck cancer, and colon cancer.

Depending on the nature of the cancer, an appropriate patient sample is obtained. As used herein, the phrase "cancerous tissue sample" refers to any cells obtained from a cancerous tumor. In the case of solid tumors, a tissue sample from the surgically removed tumor will typically be obtained and prepared for testing by conventional techniques. Alternatively, a body fluid sample, such as lymph, blood or serum sample, or an exudate fluid sample such as the cancerous organ exudate (e.g., exudate from the breast) may be collected and used as the sample to be analyzed. In the case of leukemias, lymphocytes or leukemic cells will be obtained and appropriately prepared. Similarly, in the case of any metastasized cancer, cells may be drawn from a body fluid such as lymphatic fluid, blood, serum, or a distally infected organ or exudate thereof.

The "pathology" of cancer includes all phenomena that compromise the well-being of the patient. This includes, without limitation, abnormal or uncontrollable cell growth, metastasis, interference with the normal functioning of neighboring cells, release of cytokines or other secretory products at abnormal levels, suppression or aggravation of inflammatory or immunological response, neoplasia, premalignancy, malignancy, invasion of surrounding or distant tissues or organs, such as lymph nodes, etc.

The term "diagnosis" is used herein to refer to the identification of a molecular or pathological state, disease or condition, such as the identification of a molecular subtype of breast cancer, prostate cancer, or other type of cancer.

The term "prognosis" is used herein to refer to the prediction of the likelihood of cancer-attributable death or progression, including recurrence, metastatic spread, and drug resistance, of a neoplastic disease, such as lung, colon, skin or esophageal cancer. The term "prediction" is used herein to refer to the act of foretelling or estimating, based on observation, experience, or scientific reasoning. In one example, a physician may predict the likelihood that a patient will survive, following surgical removal of a primary tumor and/or chemotherapy for a certain period of time without cancer recurrence.

As used herein, the term "correlates," or "correlates with," and like terms, refers to a statistical association between instances of two events, where events include numbers, data sets, and the like. For example, when the events involve numbers, a positive correlation (also referred to herein as a "direct correlation") means that as one increases, the other increases as well. A negative correlation (also referred to herein as an "inverse correlation") means that as one increases, the other decreases.

The term "isolated" is intended to mean that a compound is separated from all or some of the components that accompany it in nature. "Isolated" also refers to the state of a compound (e.g. protein) separated from all or some of the components that accompany it during manufacture (e.g., chemical synthesis, recombinant expression, culture medium, and the like).

A "biological sample" encompasses a variety of sample types obtained from an individual. The definition encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents; washed; or enrichment for certain cell populations, such as cancer cells. The definition also includes sample that have been enriched for particular types of molecules, e.g., nucleic acids, polypeptides, etc. The term "biological sample" encompasses a clinical sample, and also includes tissue obtained by surgical resection, tissue obtained by biopsy, cells in culture, cell supernatants, cell lysates, tissue samples, organs, bone marrow, blood, plasma, serum, and the like. A "biological sample" includes a sample obtained from a patient's cancer cell, e.g., a sample comprising polynucleotides and/or polypeptides that is obtained from a patient's cancer cell (e.g., a cell lysate or other cell extract comprising polynucleotides and/or polypeptides); and a sample comprising cancer cells from a patient. A biological sample comprising a cancer cell from a patient can also include non-cancerous cells.

DESCRIPTION OF THE SPECIFIC EMBODIMENTS

Antibodies that specifically bind to c-Met are disclosed herein, as well as related compositions and methods of use thereof. Methods of use encompass cancer therapies and diagnostics.

The antibodies contain at least one, two, or all three CDRs of the $V_H$ of the antibody from clone 1, 20, or 21. The antibodies also encompass those containing at least one, two, or all three CDRs of the $V_L$ of the antibody from clone 1, 20, or 21. Each $V_H$ or $V_L$ CDR may be independently selected. Alternatively, the antibodies compete for binding to c-Met with (e.g., bind to the same epitope as) an antibody from clone 1, 20, or 21.

An antibody of the present disclosure may also contain all $V_H$ CDRs and/or $V_L$ CDRs of an antibody from clone 1, 20, or 21. The antibodies may contain full-length $V_H$ chains of an antibody from clone 1, 20, or 21. The antibodies can also contain full-length $V_L$ chains of an antibody from clone 1, 20, or 21.

The antibody may be a single chain Fv (scFv), a Fab, a (Fab')$_2$, an (ScFv)$_2$, and the like. The antibody may be an IgG (e.g., IgG$_2$) or any other isotype, or may be a bispecific antibody.

The antibodies may be conjugated, such as to an anticancer drug, a label, a moiety that improves serum half-life (e.g. PEG), endocytosis, etc. The antibody may also be in a pharmaceutically acceptable excipient (e.g., in a unit dosage formulation). The present disclosure also provides compositions that include one or more different antibodies selected from the antibodies described herein and/or antibodies comprising one or more CDRs from these antibodies, and/or one or more antibodies comprising mutants or derivatives of these antibodies. The composition may include one or more antibodies, such as clone 1, 20, or 21.

Methods of the present disclosure include those that provide for administering one or more subject antibodies as disclosed herein in an amount effective to treat a subject having cancer expressing the antigen bound by the subject antibodies. The antibodies provided by this disclosure can also be used for diagnosis/prognosis of cancer.

Nucleic acids provided herein encode one or more antibodies that are described herein. Host cells containing such nucleic acids are also provided herein, as well as those that produce the subject antibodies (e.g. by secretion). Kits are also provided for preparing compositions containing the subject antibodies or for carrying out the subject methods.

Antibodies

Preferred antibodies have a high affinity to c-Met, which is a membrane receptor that can be exposed on the cell surface of cancer cells. Cancer cells, for example, include those derived from lung cancer cells (e.g. H1993 or H441) and others. The subject antibodies include those antibodies that are internalized into the cell upon binding to antigen, e.g., an antigen on the surface of a living mammalian cell, e.g. by endocytosis, such as receptor-mediated endocytosis.

The subject antibodies include those that competitively bind to an epitope of c-Met with an antibody from clone 1, 20, or 21. The ability of a particular antibody to recognize the same epitope as another antibody can be determined by the ability of one antibody to competitively inhibit binding of the second antibody to the antigen (e.g., as determined by competitive binding assays). The subject antibodies that bind to the same epitope as antibodies from clone 1, 20, or 21 are also contemplated herein.

Any of a number of competitive binding assays can be used to measure competition between two antibodies to the same antigen. For example, a sandwich ELISA assay can be used for this purpose. Means of assaying for cross-reactivity are well known to those of skill in the art (see, e.g., Dowbenko et al. (1988) *J. Virol.* 62: 4703-4711).

An antibody is considered to competitively inhibit binding of a second antibody, if binding of the second antibody to the antigen is reduced by at least 30%, usually at least about 40%, 50%, 60% or 75%, and often by at least about 90%, in the presence of the first antibody using any of the assays used to assess competitive binding.

This can be ascertained by providing one or more isolated target antigen (e.g. full-length c-Met or fragment thereof), attached to a solid support (e.g. using surface plasmon resonance) and assaying the ability of an antibody to bind to the target or to compete with an antibody described herein for binding to the target.

The epitope bound by anti-c-Met antibodies (e.g. clones 1 and 20) reside in the binding site for c-Met ligand (e.g. hepatocyte growth factor). The binding site for hepatocyte growth factor is in a contiguous amino acid sequence of c-Met from about residue position 25-567. The epitope can also be described by its location within the SEMA and PSI domains.

Alternatively, the epitope bound by anti-c-Met antibodies (e.g. clone 21) reside in a contiguous amino acid sequence of c-Met from about residue position 567 to about position 932. The epitope can also be described by its location in the IgG-like domain of c-Met.

The residue position numbers of c-Met used above are based on the sequence set forth in GenBank Accession No. NP_000236.2 or UniProt Accession No. P08581.

Antigens that share similar epitopes as c-Met can also be binding targets of subject antibodies. When bound to c-Met, a subject antibody can be internalized by the cell expressing the c-Met protein.

Epitopes for which anti-c-Met antibodies have affinity are cell-surface exposed and solvent-accessible on many cancer cells, particularly on the plasma membrane of cells. The epitopes can be accessible to the subject antibodies when the cells are live. For example, the epitopes may be present on cancer cells derived from lung, kidney, liver, stomach, breast, and brain, etc. Cancers cells for which anti-c-Met antibodies have affinity may be any cancer that contains a c-Met-expressing cancer cell.

As noted above, the subject antibodies encompass those that compete with one or more of the antibodies from clone 1, 20, or 21, etc. In addition, the antibodies can have a binding affinity comparable to or greater than an antibody having a $K_D$ of about $1 \times 10^{-6}$ M with c-Met. The $K_D$ of the antibodies of the present disclosure to c-Met can range from about $1 \times 10^{-6}$ M to about $1 \times 10^{-7}$ M, from about $1 \times 10^{-7}$ M to about $1 \times 10^{-8}$, from about $1 \times 10^{-8}$ M to about $1 \times 10^{-9}$ M. For example the $K_D$ of the antibodies of the present disclosure may be between about $5 \times 10^{-9}$ M to about $2 \times 10^{-8}$ M.

Examples of subject antibodies encompass those that have the same binding specificities and comprise at least two CDRs that each independently shares at least about 80%, at least about 87%, at least about 93%, at least about 94%, or up to 100% amino acid sequence identity with the amino acid sequence of a $V_H$ CDR of antibodies shown in Table 1 below (e.g. $V_H$ CDR1 of clone 21). The subject antibody can also include all three CDRs from any $V_H$ CDRs of each antibody shown in Table 1, such that each $V_H$ CDR in the subject antibody is selected from a single antibody shown in Table 1 and each $V_H$ CDR independently shares at least about 80%, at least about 87%, at least about 93%, at least about 94%, or up to 100% amino acid sequence identity with the amino acid sequence of the $V_H$ CDR of the antibody shown in Table 1. For example, the heavy chain of a subject antibody can contain two $V_H$ CDRs or all three $V_H$ CDRs of clone 21. Alternatively, the heavy chain can contain two $V_H$ CDRs or all three $V_H$ CDRs of clone 21.

Similarly for the light chain, a subject antibody will have the same binding specificity and can contain at least two CDRs that are each independently at least about 80%, at least about 87%, at least about 93%, at least about 94%, or up to 100% amino acid sequence identity with the amino acid sequence of a $V_L$ CDR of each antibody shown in Table 1 (e.g. $V_L$ CDR1 of clone 21). The subject antibody can also include all three $V_L$ CDRs from any of the antibodies shown in Table 1 and each $V_L$ CDR independently shares at least about 80%, at least about 87%, at least about 93%, at least about 94%, or up to 100% amino acid sequence identity with the amino acid sequence of the $V_L$ CDR of the antibody shown in Table 1. For example, the light chain of a subject antibody can contain two $V_L$ CDRs or all three $V_L$ CDRs of clone 21. Alternatively, the light chain can contain two $V_L$ CDRs or all three $V_L$ CDRs of clone 21.

Optionally, antibodies can contain the same (i.e. 100% identity), similar, or different framework sequences (FR) in any of corresponding framework sequences in the heavy or light chain provided in Table 1. Where the framework sequences are similar, the framework may be at least about 85%, at least about 86%, at least about 90%, at least about 93%, at least about 96%, at least about 98%, or up to 100% identity to a corresponding framework sequence in any of antibodies shown in Table 1 below.

An antibody of the present disclosure may therefore contain a full-length $V_H$ and/or full length $V_L$ sequence that has at least 80% identity, at least 85%, at least 90%, at least 95%, up to 100% amino acid sequence identity to a full-length $V_H$ or $V_L$ sequence shown in Table 1. For example, a subject antibody can contain the full length $V_H$ and/or full length $V_L$ of clone 21. Alternatively, the subject antibody can contain the full length $V_H$ and/or full length $V_L$ of clone 20.

Method of Antibody Production

Using the information provided herein, the anti-c-Met antibodies of the present disclosure are prepared using standard techniques well known to those of skill in the art. For example, the polypeptide sequences provided herein (see, e.g., Table 1) can be used to determine appropriate nucleic acid sequences encoding the antibodies and the nucleic acids sequences then used to express one or more antibodies specific for c-Met. The nucleic acid sequence(s) can be optimized to reflect particular codon "preferences" for various expression systems according to standard methods well known to those of skill in the art.

Using the sequence information provided, the nucleic acids may be synthesized according to a number of standard methods known to those of skill in the art. Oligonucleotide synthesis is preferably carried out on commercially available solid phase oligonucleotide synthesis machines or manually synthesized using, for example, the solid phase phosphoramidite triester method.

Once a nucleic acid encoding a subject antibody is synthesized it can be amplified and/or cloned according to standard methods. Molecular cloning techniques to achieve these ends are known in the art. A wide variety of cloning and in vitro amplification methods suitable for the construction of recombinant nucleic acids are known to persons of skill in the art.

Expression of natural or synthetic nucleic acids encoding the antibodies of the present disclosure can be achieved by operably linking a nucleic acid encoding the antibody to a promoter (which is either constitutive or inducible), and incorporating the construct into an expression vector. The vectors can be suitable for replication and integration in prokaryotes, eukaryotes, or both. Typical cloning vectors contain transcription and translation terminators, initiation sequences, and promoters useful for regulation of the expression of the nucleic acid encoding the antibody. The vectors optionally contain generic expression cassettes containing at least one independent terminator sequence, sequences permitting replication of the cassette in both eukaryotes and prokaryotes, i.e., shuttle vectors, and selection markers for both prokaryotic and eukaryotic systems.

To obtain high levels of expression of a cloned nucleic acid it is common to construct expression plasmids which typically contain a strong promoter to direct transcription, a ribosome binding site for translational initiation, and a transcription/translation terminator. The inclusion of selection markers in DNA vectors transformed in *E. coli* is also useful. Examples of such markers include genes specifying resistance to ampicillin, tetracycline, or chloramphenicol. Expression systems for expressing antibodies are available using, for example, *E. coli, Bacillus* sp. and *Salmonella. E. coli* systems may also be used.

The antibody gene(s) may also be subcloned into the expression vector that allows for the addition of a tag (e.g. hexahistidine) at the C-terminal end or the N-terminal end of the antibody (e.g. scFv) to facilitate purification. Methods of transfecting and expressing genes in mammalian cells are known in the art. Transducing cells with nucleic acids can involve, for example, incubating viral vectors containing nucleic acids with cells within the host range of the vector. The culture of cells used in the present disclosure, including cell lines and cultured cells from tissue or blood samples is well known in the art.

Once the nucleic acid for a subject antibody is isolated and cloned, one can express the nucleic acid in a variety of recombinantly engineered cells known to those of skill in the art. Examples of such cells include bacteria, yeast, filamentous fungi, insect (e.g. those employing baculoviral vectors), and mammalian cells.

Isolation and purification of a subject antibody can be accomplished according to methods known in the art. For example, a protein can be isolated from a lysate of cells genetically modified to express the protein constitutively and/or upon induction, or from a synthetic reaction mixture, by immunoaffinity purification (or precipitation using Protein G or A), washing to remove non-specifically bound material, and eluting the specifically bound antibody. The isolated antibody can be further purified by dialysis and other methods normally employed in protein purification methods. In one embodiment, the antibody may be isolated using metal chelate chromatography methods. Antibodies of the present disclosure may contain modifications to facilitate isolation, as discussed above.

The subject antibodies may be prepared in substantially pure or isolated form (e.g., free from other polypeptides). The protein can present in a composition that is enriched for the polypeptide relative to other components that may be present (e.g., other polypeptides or other host cell components). Purified antibodies may be provided such that the antibody is present in a composition that is substantially free of other expressed proteins, e.g., less than 90%, usually less than 60% and more usually less than 50% of the composition is made up of other expressed proteins.

The present disclosure also provides cells that produce subject antibodies. The cells can be a hybrid cell or "hybridoma" that is capable of reproducing antibodies in vitro (e.g. monoclonal antibodies, such as IgG).

Techniques for creating recombinant DNA versions of the antigen-binding regions of antibody molecules which bypass the generation of hybridomas are also contemplated herein. DNA is cloned into a bacterial (e.g., bacteriophage), yeast, insect or mammalian expression system, for example. One example of a suitable technique uses a bacteriophage lambda vector system having a leader sequence that causes the expressed antibody (e.g. Fab or scFv) to migrate to the periplasmic space (between the bacterial cell membrane and the cell wall) or to be secreted. One can rapidly generate a great numbers of functional fragments (e.g. scFv) for those which bind c-Met.

Modification

The present disclosure encompasses antibodies and nucleic acids that are modified to provide a desired feature, e.g., to facilitate delivery to a specific type of tissue and/or cells in a subject, to increase serum half-life, to supplement anti-cancer activity, etc. The antibodies of the present disclosure can be provided with or without modification, and include human antibodies, humanized antibodies, and chimeric antibodies. One way to modify a subject antibody is to conjugate (e.g. link) one or more additional elements at the N- and/or C-terminus of the antibody, such as another protein and/or a drug or carrier molecule.

A subject antibody modified with a conjugate retains the desired binding specificity, while exploiting properties of the second molecule of the conjugate to impart an additional desired characteristic. For example, a subject antibody can be conjugated to a second molecule that aids in solubility, storage or other handling properties, cell permeability, half-life, reduction in immunogenicity, controls release and/or distribution such as by targeting a particular cell (e.g., neurons, leucocytes, tumor cells, etc.) or cellular location (e.g., lysosome, endosome, mitochondria etc.), tissue or other bodily location (e.g., blood, neural tissue, particular organs etc.). Other examples include the conjugation of a dye, fluorophore or other detectable labels or reporter molecules for assays, tracking and the like. More specifically, a subject antibody can be conjugated to a second molecule such as a peptide, polypeptide, dye, fluorophore, nucleic acid, carbohydrate, anti-cancer agent, lipid and the like (e.g., at either the reducing or non-reducing end), such as the attachment of a lipid moiety, including N-fatty acyl groups such as N-oleoyl, fatty amines such as dodecyl amine, oleoyl amine, and the like.

For example, given that the antibodies can be internalized into cells, the antibody or nucleic acids of the present disclosure may be further modified to increase or decrease the efficiency of delivery into cells. Gene delivery methods are also contemplated herein to deliver nucleic acids that express the subject antibodies in cells. The efficiency of cellular uptake (e.g. endocytosis) of antibodies can be increased or decreased by linking to peptides or proteins. For example, a given antibody can be linked to a ligand for a target receptor or large molecule that is more easily engulfed by endocytotic mechanisms, such as another antibody. The conjugate payload can also be released by acid hydrolysis or enzymatic activity when the endocytotic vesicle fuses with lysosomes. To decrease cellular uptake, the conjugate can include a ligand that retains the antibody on the surface of a cell, which can be useful as a control for cellular uptake, or in some instances decrease uptake in one cell type while increasing it in others.

Other features of a conjugated antibody may include one where the conjugate reduces toxicity relative to unconjugated antibody. Another feature is that the conjugate may target a type of cell or organ (e.g. cancerous cell or cancerous tissue) more efficiently than an unconjugated antibody.

Additional examples include an antibody conjugated with one or more molecules that complement, potentiate, enhance or can otherwise operate synergistically in connection with the antibody. The antibody can have attached an anti-cancer drug, e.g., for delivery to a site of a cancer to further facilitate cell killing or clearance, e.g., an anti-proliferation moiety (e.g., a VEGF antagonist, e.g., an anti-VEGF antibody), a toxin (e.g., doxorubincin, ricin, *Pseudomonas* exotoxin A, and the like), a radionuclide (e.g. $^{90}Y$, $^{131}I$, $^{171}L$, $^{10}B$ for boron neutron capture, and the like), an anti-cancer agent, and/or an oligonucleotide (e.g. siRNA).

Antibody-Containing Liposome.

For example, an antibody may be formulated in a lipidic nanoparticle (e.g., a liposome) by covalent or non-covalent modifications. The antibody may be attached to the surface of a lipidic nanoparticle directly via an Fc region, for example. The antibody may also be covalently attached to a terminus of a polymer grafted at the surface of a lipidic nanoparticle via a linker. Such conjugated lipidic nanoparticles may be referred to herein as "immunoliposomes".

A gene encoding the antibody of the present disclosure (e.g. S20) can be fused with a cysteine at C-terminal created. This cysteine fusion protein can then be specifically coupled through its c-terminal cysteine to maleimide-modified PEG chains on external surface of liposome via site-directed conjugation. The immunoliposomes can be loaded with one or more of the anti-cancer agents, such as small molecule, peptide, and/or nucleic acid (e.g. siRNAs) or any known in the art. The liposome can contain anti-cancer drugs, such as doxorubicin, for example. The subject antibodies in an immunoliposome can act as a targeting moiety enabling the immunoliposomes to specifically bind to c-Met on the surface of cancer cells. Methods of making and loading lipidic nanoparticles, such as liposomes and immunoliposomes, are known in the art. See, for example, U.S. Pat. No. 7,749,485 and US 20070031484, disclosures of which are incorporated herein by reference.

The antibodies of the present disclosure can optionally be modified to provide for improved pharmacokinetic profile (e.g., by PEGylation, hyperglycosylation, and the like). Modifications that can enhance serum half-life are of interest. A subject antibody may be "PEGylated", as containing one or more poly(ethylene glycol) (PEG) moieties. Methods and reagents suitable for PEGylation of a protein are well known in the art and may be found in U.S. Pat. No. 5,849,860, disclosure of which is incorporated herein by reference.

Where the subject antibody is to be isolated from a source, the subject protein can be conjugated to moieties the facilitate purification, such as members of specific binding pairs, e.g., biotin (member of biotin-avidin specific binding pair), a lectin, and the like. A subject protein can also be bound to (e.g., immobilized onto) a solid support, including, but not limited to, polystyrene plates or beads, magnetic beads, test strips, membranes, and the like.

Where the antibodies are to be detected in an assay, the subject proteins may also contain a detectable label, e.g., a radioisotope (e.g., $^{125}$I; $^{35}$S, and the like), an enzyme which generates a detectable product (e.g., luciferase, β-galactosidase, horse radish peroxidase, alkaline phosphatase, and the like), a fluorescent protein, a chromogenic protein, dye (e.g., fluorescein isothiocyanate, rhodamine, phycoerythrin, and the like); fluorescence emitting metals, e.g., $^{152}$Eu, or others of the lanthanide series, attached to the protein through metal chelating groups such as EDTA; chemiluminescent compounds, e.g., luminol, isoluminol, acridinium salts, and the like; bioluminescent compounds, e.g., luciferin; fluorescent proteins; and the like. Indirect labels include antibodies specific for a subject protein, wherein the antibody may be detected via a secondary antibody; and members of specific binding pairs, e.g., biotin-avidin, and the like.

Any of the above elements that are used to modify the subject antibody may be linked to the antibody via a linker, e.g. a flexible linker. If present, the linker molecules are generally of sufficient length to permit the antibody and a linked carrier to allow some flexible movement between the antibody and the carrier. The linker molecules are generally about 6-50 atoms long. The linker molecules may also be, for example, aryl acetylene, ethylene glycol oligomers containing 2-10 monomer units, diamines, diacids, amino acids, or combinations thereof.

Where the linkers are peptide, the linkers can be of any of a suitable of different lengths, such as from 1 amino acid (e.g., Gly) to 20 or more amino acids, from 2 amino acids to 15 amino acids, from 3 amino acids to 12 amino acids, including 4 amino acids to 10 amino acids, 5 amino acids to 9 amino acids, 6 amino acids to 8 amino acids, or 7 amino acids to 8 amino acids, and may be 1, 2, 3, 4, 5, 6, or 7 amino acids.

Flexible linkers include glycine polymers $(G)_n$, glycine-serine polymers (including, for example, $(GS)_n$, $GSGGS_n$ (SEQ ID NO: 1) and $GGGS_n$ (SEQ ID NO: 2), where n is an integer of at least one), glycine-alanine polymers, alanine-serine polymers, and other flexible linkers known in the art. Glycine and glycine-serine polymers may be used where relatively unstructured amino acids are of interest, and may serve as a neutral tether between components. Examples of flexible linkers include, but are not limited GGSG (SEQ ID NO:3), GGSGG (SEQ ID NO:4), GSGSG (SEQ ID NO: 5), GSGGG (SEQ ID NO: 6), GGGSG (SEQ ID NO: 7), GSSSG (SEQ ID NO: 8), and the like. The ordinarily skilled artisan will recognize that design of a peptide conjugated to any elements described above can include linkers that are all or partially flexible, such that the linker can include a flexible linker as well as one or more portions that confer less flexible structure.

Human Engineered Antibody.

The antibodies of the present disclosure can be in a form of an immunoglobulin, such as a human IgG. For example, an antibody of the present disclosure in a form of scFV may be linked to a human constant region (e.g. Fc region) to be made into a human immunoglobulin, e.g. an intact IgG immunoglobulin.

Fc Region.

An antibody of the present disclosure that binds c-Met may contain an Fc region. The Fc region may be any of the naturally occurring isoforms found in human or other animals (e.g. derived from any classes or subclasses of immunoglobulins) and can optionally be further modified to have altered function. Where the Fc region is non-human and the CDR and/or FR regions are human, the antibodies may be described as a chimeric antibody. The Fc region may be modified in one or more amino acid residue position to have increased effector functions, such as initiating cell-mediated cytotoxicity or activating complement activity (e.g. C1q binding or complement dependent cytotoxicity), downregulating cell-surface receptor, etc. Details of Fc variants that may be used as antibodies of the present disclosure may be found in, for example, U.S. Pat. No. 7,416,727, U.S. Pat. No. 7,371,826, U.S. Pat. No. 7,335,742, U.S. Pat. No. 7,355,008, U.S. Pat. No. 7,521,542, and U.S. Pat. No. 7,632,497, disclosures of which are incorporated herein by reference.

Compositions

The subject compositions provide antibodies and/or nucleic acid encoding thereof, in which the antibodies bind to cancer cells expressing c-Met and are internalized by the cancer cells. The compositions of the present disclosure find use in treating a subject (e.g., a human) containing cancer, and may be suitable for treatment during any stage of the disease.

Compositions containing one, two, or more different antibodies can be provided as a pharmaceutical composition and administered to a mammal (e.g., to a human) in need thereof. Compositions contemplated herein may contain one, two, three, or more different antibodies of the present disclosure (and/or nucleic acids encoding thereof). For example, the composition can contain one or more of the following: clones 1, 2, and 3. The composition may optionally further include antibodies containing one or more CDRs from these antibodies, and/or one or more antibodies containing mutants or derivatives of these antibodies.

An example of a composition of the present disclosure may include any of the antibodies disclosed in Table 1. Where the composition contains two or more antibodies, each antibody can be specific to the same or different epitopes or to epitopes on different antigens. For example, the composition may contain at least one antibody specific for the epitope of c-Met and another antibody specific for another cell-surface antigen, such as EGFR. The composition may also contain dual-specific, polyspecific antibodies, or nucleic acids encoding thereof.

The antibodies of the present disclosure can be used individually, and/or in combination with each other (e.g. to form bispecific or polyspecific antibodies), and/or in combination with other known anti-cancer agents (e.g. antibodies for cancer treatment). For example, a composition, such as a liposome, can comprise two or more antibodies, in which at least one of the antibodies is an antibody of the present disclosure. As described above, the liposome may contain one or more antibodies that are different than the subject antibodies. Such liposome may be dual-specific, polyspecific, etc, so that the liposome is specific for an additional epitope in addition to the epitope of the subject antibody.

Combinations can be provided in a single formulation or can be provided as separate formulations in a kit, where the separate formulations may contain a single antibody or two antibodies. Such separate formulations of a kit may be combined prior to administration or administered by separate injection.

A subject pharmaceutical composition can be provided in a pharmaceutically acceptable excipient, which can be a solution such as an aqueous solution, often a saline solution or they can be provided in powder form. A subject composition may comprise other components, such as pharmaceutical grades of mannitol, lactose, starch, magnesium stearate, sodium saccharin, talcum, cellulose, glucose, sucrose, magnesium, carbonate, and the like. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like.

A subject antibody, e.g., in the form of a pharmaceutically acceptable salt, can be formulated for oral, topical or parenteral administration for use in the methods described later below. In certain embodiments, e.g., where an antibody is administered as a liquid injectable, an antibody formulation is provided as a ready-to-use dosage form, or as a reconstitutable storage-stable powder or liquid composed of pharmaceutically acceptable carriers and excipients.

Compositions of the present disclosure can include a therapeutically effective amount of a subject antibody, as well as any other compatible components, as needed. By "therapeutically effective amount" is meant that the administration of that amount to an individual, either in a single dose, as part of a series of the same or different antibody or compositions, is effective to reduce the proliferation and/or metastases of a cancerous cell in a subject. Such therapeutically effective amount of an antibody and its impact on cell growth includes cooperative and/or synergistic inhibition of cell growth in conjunction with one or more other therapies (e.g., immunotherapy, chemotherapy, radiation therapy etc.) As noted below, the therapeutically effective amount can be adjusted in connection with dosing regimen and diagnostic analysis of the subject's condition (e.g., monitoring for the presence or absence of a cell surface epitopes using an antibody specific for c-Met) and the like.

Amount and Dosage.

The concentration of an antibody in a pharmaceutical formulations can vary from less than about 0.1%, usually at or at least about 2% to as much as 20% to 50% or more by weight, and will be selected primarily by fluid volumes, viscosities, etc., in accordance with the particular mode of administration selected and the patient's needs. The resulting compositions may be in the form of a solution, suspension, tablet, pill, capsule, powder, gel, cream, lotion, ointment, aerosol or the like.

Also, suitable doses and dosage regimens can be determined by comparisons to anticancer or immunosuppressive agents that are known to affect the desired growth inhibitory or immunosuppressive response. Such dosages include dosages which result in the low dose inhibition of cell growth, without significant side effects. In proper doses and with suitable administration of certain compounds, the compounds of the present disclosure can provide for a wide range of intracellular effects, e.g., from partial inhibition to essentially complete inhibition of cell growth. Dosage treatment may be a single dose schedule or a multiple dose schedule (e.g., including ramp and maintenance doses). As indicated below, a subject composition may be administered in conjunction with other agents, and thus doses and regiments can vary in this context as well to suit the needs of the subject.

Combination Therapy

Any of a wide variety of cancer therapies can be combined in a composition with a subject antibody. For example, agents used in chemotherapeutic treatment or biological response modifier treatment may be present in the pharmaceutical composition comprising the antibody, such as an immunoliposome. Certain agents that can be used in combination with the subject antibodies are briefly discussed below.

Chemotherapeutic agents are non-peptidic (i.e., non-proteinaceous) compounds that reduce proliferation of cancer cells, and encompass cytotoxic agents and cytostatic agents. Non-limiting examples of chemotherapeutic agents include alkylating agents, nitrosoureas, antimetabolites, antitumor antibiotics, plant (e.g., vinca) alkaloids, nucleic acids, such as inhibitory nucleic acids (e.g. siRNA), and steroid hormones.

Antimetabolite agents include folic acid analogs, pyrimidine analogs, purine analogs, and adenosine deaminase inhibitors, for example.

Suitable natural products and their derivatives, (e.g., vinca alkaloids, antitumor antibiotics, enzymes, lymphokines, and epipodophyllotoxins) can be used as anti-cancer agents. E.g. Taxanes, such as paclitaxel, as well as any active taxane derivative or pro-drug.

Other anti-proliferative cytotoxic agents are navelbene, CPT-11, anastrazole, letrazole, capecitabine, reloxafine, cyclophosphamide, ifosamide, and droloxafine. Microtubule affecting agents that have antiproliferative activity are also suitable for use. Hormone modulators and steroids (including synthetic analogs) that are suitable for use.

Method of Treatment

A method is also disclosed herein for reducing proliferation of cancer cells by administering an antibody of the present disclosure. Subjects having, suspected of having, or at risk of developing cancer are contemplated for therapy and diagnosis described herein.

The method involves administering a therapeutically effective amount of an anti-c-Met antibody to a patient in need thereof. Administration of the antibody can inhibit cancer cell proliferation, reduce tumor weight, reduce metastases, and/or improve the clinical outcome in patients.

The present method finds use in a variety of cancer therapies (including cancer prevention and post-diagnosis cancer therapy) in a mammalian subject, particularly in a human. Subjects having, suspected of having, or at risk of developing a tumor are contemplated for therapy described herein.

In a related embodiment, the subject being treated possesses cells that express (e.g. overexpresses) c-Met. c-Met is expressed on the cancer cell surface and is often present at a higher level than a corresponding non-cancerous cell. This aspect can be beneficial in the context of the methods of the present disclosure in that cells expressing or presenting c-Met can be amenable to treatment with an antibody of the present disclosure. The antibody can be administered to a subject, for example, where therapy is initiated at a point where presence of the antigen is not detectable, and thus is not intended to be limiting. It is also possible to initiate antibody therapy prior to the first sign of disease symptoms, at the first sign of possible disease, or prior to or after diagnosis of a disease.

For example, the cancers that can be inhibited by the method of the present disclosure include, but are not limited to, carcinomas, including adenocarcinomas, and particularly lung carcinomas (non-small cell and small cell). Other cancers that can be treated include those that originate from cancerous growth in brain, colorectal, gastric, head and neck, stomach, kidney, liver, and breast.

Types of Cancer

The methods are useful in the context of treating or preventing a wide variety of cancers, particularly cancers that involve formation of new blood vessels and metastatic cancers. Examples of cancers amenable for therapy using the methods of the present disclosure are provided below.

Carcinomas that can be amenable to therapy by a method disclosed herein include, but are not limited to, esophageal carcinoma, hepatocellular carcinoma, basal cell carcinoma (a form of skin cancer), squamous cell carcinoma (various tissues), bladder carcinoma, including transitional cell carcinoma (a malignant neoplasm of the bladder), bronchogenic carcinoma, colon carcinoma, colorectal carcinoma, gastric carcinoma, lung carcinoma, including small cell carcinoma and non-small cell carcinoma of the lung, adrenocortical carcinoma, thyroid carcinoma, pancreatic carcinoma, breast carcinoma, ovarian carcinoma, prostate carcinoma, adenocarcinoma, sweat gland carcinoma, sebaceous gland carcinoma, papillary carcinoma, papillary adenocarcinoma, cystadenocarcinoma, medullary carcinoma, renal cell carcinoma, ductal carcinoma in situ or bile duct carcinoma, choriocarcinoma, seminoma, embryonal carcinoma, Wilm's tumor, cervical carcinoma, uterine carcinoma, testicular carcinoma, osteogenic carcinoma, epithelieal carcinoma, and nasopharyngeal carcinoma.

Sarcomas that can be amenable to therapy by a method disclosed herein include, but are not limited to, fibrosarcoma, myxosarcoma, liposarcoma, chondrosarcoma, chordoma, osteogenic sarcoma, osteosarcoma, angiosarcoma, endotheliosarcoma, lymphangiosarcoma, lymphangioendotheliosarcoma, synovioma, mesothelioma, Ewing's sarcoma, leiomyosarcoma, rhabdomyosarcoma, and other soft tissue sarcomas.

Other solid tumors that can be amenable to therapy by a method disclosed herein include, but are not limited to, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

Other cancers that can be amenable to treatment according to the methods disclosed herein include atypical meningioma (brain), islet cell carcinoma (pancreas), medullary carcinoma (thyroid), mesenchymoma (intestine), hepatocellular carcinoma (liver), hepatoblastoma (liver), clear cell carcinoma (kidney), and neurofibroma mediastinum.

Further exemplary cancers that can be amenable to treatment using a methods disclosed herein include, but are not limited to, cancers of neuroectodermal and epithelial origin. Examples of cancers of neuroectodermal origin include, but are not limited to, Ewings sarcoma, spinal tumors, brain tumors, supratenbrial primative neuroectodermal tumors of infancy, tubulocystic carcinoma, mucinous tubular and spindle cell carcinoma, renal tumors, mediastinum tumors, neurogliomas, neuroblastomas, and sarcomas in adolescents and young adults. Examples of epithelial origin include, but are not limited to, small cell lung cancer, cancers of the breast, eye lens, colon, pancreas, kidney, liver, ovary, and bronchial epithelium.

Combinations with Other Cancer Therapies

Therapeutic administration of an anti-c-Met antibody can include administration as a part of a therapeutic regimen that may or may not be in conjunction with additional standard anti-cancer therapeutics, including but not limited to immunotherapy, chemotherapeutic agents and surgery (e.g., as those described further below).

In addition, therapeutic administration of the anti-c-Met antibody can also be post-therapeutic treatment of the subject with an anti-cancer therapy, where the anti-cancer therapy can be, for example, surgery, radiation therapy, administration of chemotherapeutic agents, and the like. Cancer therapy using fibrillar proteins of the present disclosure can also be used in combination with immunotherapy. In other examples, the fibrillar proteins can be administered in combination with one or more chemotherapeutic agents (e.g., cyclophosphamide, doxorubicin, vincristine and prednisone (CHOP)), and/or in combination with radiation treatment and/or in combination with surgical intervention (e.g., pre- or post-surgery to remove a tumor). Where the fibrillar proteins are used in connection with surgical intervention, the fibrillar protein can be administered prior to, at the time of, or after surgery to remove cancerous cells, and may be administered systemically or locally at the surgical site. The fibrillar protein alone or in combinations described above can be administered systemically (e.g., by parenteral administration, e.g., by an intravenous route) or locally (e.g., at a local tumor site, e.g., by intratumoral administration (e.g., into a solid tumor, into an involved lymph node in a lymphoma or leukemia), administration into a blood vessel supplying a solid tumor, etc.).

Any of a wide variety of cancer therapies can be used in combination with the fibrillar protein therapies described herein. Such cancer therapies include surgery (e.g., surgical removal of cancerous tissue), radiation therapy, bone marrow transplantation, chemotherapeutic treatment, biological response modifier treatment, and certain combinations of the foregoing.

Radiation therapy includes, but is not limited to, X-rays or gamma rays that are delivered from either an externally applied source such as a beam, or by implantation of small radioactive sources.

Chemotherapeutic agents are non-peptidic (i.e., non-proteinaceous) compounds that reduce proliferation of cancer cells, and encompass cytotoxic agents and cytostatic agents. Non-limiting examples of chemotherapeutic agents include alkylating agents, nitrosoureas, antimetabolites, antitumor antibiotics, plant (vinca) alkaloids, and steroid hormones.

Agents that act to reduce cellular proliferation are known in the art and widely used. Such agents include alkylating agents, such as nitrogen mustards, nitrosoureas, ethylenimine derivatives, alkyl sulfonates, and triazenes, including, but not limited to, mechlorethamine, cyclophosphamide (CYTOXAN™), melphalan (L-sarcolysin), carmustine (BCNU), lomustine (CCNU), semustine (methyl-CCNU), streptozocin, chlorozotocin, uracil mustard, chlormethine, ifosfamide, chlorambucil, pipobroman, triethylenemelamine, triethylenethiophosphoramine, busulfan, dacarbazine, and temozolomide.

Antimetabolite agents include folic acid analogs, pyrimidine analogs, purine analogs, and adenosine deaminase inhibitors, including, but not limited to, cytarabine (CYTOSAR-U), cytosine arabinoside, fluorouracil (5-FU), floxuridine (FudR), 6-thioguanine, 6-mercaptopurine (6-MP), pentostatin, 5-fluorouracil (5-FU), methotrexate, 10-propargyl-5,8-dideazafolate (PDDF, CB3717), 5,8-dideazatetrahydrofolic acid (DDATHF), leucovorin, fludarabine phosphate, pentostatine, and gemcitabine.

Suitable natural products and their derivatives, (e.g., vinca alkaloids, antitumor antibiotics, enzymes, lymphokines, and epipodophyllotoxins), include, but are not limited to, Ara-C, paclitaxel (TAXOL®), docetaxel (TAXOTERE®), deoxycoformycin, mitomycin-C, L-asparaginase, azathioprine; brequinar; alkaloids, e.g. vincristine, vinblastine, vinorelbine, vindesine, etc.; podophyllotoxins, e.g. etoposide, teniposide, etc.; antibiotics, e.g. anthracycline, daunorubicin hydrochloride (daunomycin, rubidomycin, cerubidine), idarubicin, doxorubicin, epirubicin and morpholino derivatives, etc.; phenoxizone biscyclopeptides, e.g. dactinomycin; basic glycopeptides, e.g. bleomycin; anthraquinone glycosides, e.g. plicamycin (mithramycin); anthracenediones, e.g. mitoxantrone; azirinopyrrolo indolediones, e.g. mitomycin; macrocyclic immunosuppressants, e.g. cyclosporine, FK-506 (tacrolimus, prograf), rapamycin, etc.; and the like.

Other anti-proliferative cytotoxic agents are navelbene, CPT-11, anastrazole, letrazole, capecitabine, reloxafine, cyclophosphamide, ifosamide, and droloxafine.

Microtubule affecting agents that have antiproliferative activity are also suitable for use and include, but are not limited to, allocolchicine (NSC 406042), Halichondrin B (NSC 609395), colchicine (NSC 757), colchicine derivatives (e.g., NSC 33410), dolstatin 10 (NSC 376128), maytansine (NSC 153858), rhizoxin (NSC 332598), paclitaxel (TAXOL®), TAXOL® derivatives, docetaxel (TAXOTERE®), thiocolchicine (NSC 361792), trityl cysterin, vinblastine sulfate, vincristine sulfate, natural and synthetic epothilones including but not limited to, eopthilone A, epothilone B, discodermolide; estramustine, nocodazole, and the like.

Hormone modulators and steroids (including synthetic analogs) that are suitable for use include, but are not limited to, adrenocorticosteroids, e.g. prednisone, dexamethasone, etc.; estrogens and pregestins, e.g. hydroxyprogesterone caproate, medroxyprogesterone acetate, megestrol acetate, estradiol, clomiphene, tamoxifen; etc.; and adrenocortical suppressants, e.g. aminoglutethimide; 17α-ethinylestradiol; diethylstilbestrol, testosterone, fluoxymesterone, dromostanolone propionate, testolactone, methylprednisolone, methyl-testosterone, prednisolone, triamcinolone, chlorotrianisene, hydroxyprogesterone, aminoglutethimide, estramustine, medroxyprogesterone acetate, leuprolide, Flutamide (Drogenil), Toremifene (Fareston), and ZOLADEX®. Estrogens stimulate proliferation and differentiation, therefore compounds that bind to the estrogen receptor are used to block this activity. Corticosteroids may inhibit T cell proliferation.

Other chemotherapeutic agents include metal complexes, e.g. cisplatin (cis-DDP), carboplatin, etc.; ureas, e.g. hydroxyurea; and hydrazines, e.g. N-methylhydrazine; epidophyllotoxin; a topoisomerase inhibitor; procarbazine; mitoxantrone; leucovorin; tegafur; etc. Other anti-proliferative agents of interest include immunosuppressants, e.g. mycophenolic acid, thalidomide, desoxyspergualin, azasporine, leflunomide, mizoribine, azaspirane (SKF 105685); IRESSA® (ZD 1839, 4-(3-chloro-4-fluorophenylamino)-7-methoxy-6-(3-(4-morpholinyl)propoxy)quinazoline); etc.

"Taxanes" include paclitaxel, as well as any active taxane derivative or pro-drug. "Paclitaxel" (which should be understood herein to include analogues, formulations, and derivatives such as, for example, docetaxel, TAXOL, TAXOTERE (a formulation of docetaxel), 10-desacetyl analogs of paclitaxel and 3'N-desbenzoyl-3'N-t-butoxycarbonyl analogs of paclitaxel) may be readily prepared utilizing techniques known to those skilled in the art.

Paclitaxel should be understood to refer to not only the common chemically available form of paclitaxel, but analogs and derivatives (e.g., TAXOTERE™ docetaxel, as noted above) and paclitaxel conjugates (e.g., paclitaxel-PEG, paclitaxel-dextran, or paclitaxel-xylose).

In the treatment of some individuals in accordance with the method of the present disclosure, it may be desirable to use a high dose regimen in conjunction with a rescue agent for non-malignant cells. In such treatment, any agent capable of rescue of non-malignant cells can be employed, such as citrovorum factor, folate derivatives, or leucovorin. Such rescue agents are well known to those of ordinary skill in the art. Rescue agents include those which do not interfere with the ability of the present inventive compounds to modulate cellular function.

Routes of Administration

Administration of the anti-c-Met antibody may be achieved through various methods to different parts of the body, including intratumoral, intravenous, intradermal, subcutaneous, oral (e.g., inhalation), transdermal (i.e., topical), transmucosal, intraperitoneal, intraarterial, and rectal administration. Other suitable routes include administration of the composition orally, bucally, nasally, nasopharyngeally, parenterally, enterically, gastrically, topically, transdermally, subcutaneously, intramuscularly, in tablet, solid, powdered, liquid, aerosol form, intralesional injection into the tumor, intralesional injection adjacent to the tumor, intravenous infusion, and intraarterial infusion. Administration may be done locally or systemically, with or without added excipients. Administering can also be done via slow release mode at or around tumor sites of a subject.

One skilled in the art will appreciate that a variety of suitable methods of administering a formulation of the present disclosure to a subject or host, e.g., patient, in need thereof, are available, and, although more than one route can be used to administer a particular formulation, a particular route can provide a more immediate and more effective reaction than another route.

The phrase "therapeutically effective amount" refers to an amount that produces some desired effect at a reasonable benefit/risk ratio applicable to any medical treatment. The effective amount may vary depending on such factors as the disease or condition being treated, the particular targeted constructs being administered, the size of the subject, or the severity of the disease or condition. One of ordinary skill in the art may empirically determine the effective amount of a particular compound without necessitating undue experimentation.

According to exemplary implementations, the protein may be administered as part of a composition, which is described in more detail below. The composition may be in various forms including powders, creams, gels, salves, ointments, solutions, tablets, capsules, sprays, and patches. Vehicles and carriers may be used for delivery of the composition to the patient. Such carriers include solubilizing agents, diluents, and dispersion media. These carriers are biocompatible, pharmaceutically acceptable, and do not alter the treatment characteristics of the fibrillar protein. Excipients, adjuvants and other ingredients may also be included in the composition.

Dosage

In the methods, an effective amount of anti-c-Met antibody is administered to a subject in need thereof. The amount administered varies depending upon the goal of the administration, the health and physical condition of the individual to be treated, age, the taxonomic group of individual to be treated (e.g., human, non-human primate, primate, etc.), the degree of resolution desired, the formulation of the anti-c-Met antibody composition, the treating clinician's assessment of the medical situation, and other relevant factors. It is expected that the amount will fall in a relatively broad range that can be determined through routine trials. For example, the amount of anti-c-Met antibody employed to inhibit cancer metastasis is not more than about the amount that could otherwise be irreversibly toxic to the subject (i.e., maximum tolerated dose). In other cases the amount is around or even well below the toxic threshold, but still in an immunoeffective concentration range, or even as low as threshold dose.

Individual doses are typically not less than an amount required to produce a measurable effect on the subject, and may be determined based on the pharmacokinetics and pharmacology for absorption, distribution, metabolism, and excretion ("ADME") of the anti-c-Met antibody of its by-products, and thus based on the disposition of the composition within the subject. This includes consideration of the route of administration as well as dosage amount, which can be adjusted for topical (applied directly where action is desired for mainly a local effect), enteral (applied via digestive tract for systemic or local effects when retained in part of the digestive tract), or parenteral (applied by routes other than the digestive tract for systemic or local effects) applications. For instance, administration of the anti-c-Met antibody is typically via injection and often intravenous, intramuscular, intratumoral, or a combination thereof.

The anti-c-Met antibody may be administered by infusion or by local injection, e.g. by infusion at a rate of about 50 mg/h to about 400 mg/h, including about 75 mg/h to about 375 mg/h, about 100 mg/h to about 350 mg/h, about 150 mg/h to about 350 mg/h, about 200 mg/h to about 300 mg/h, about 225 mg/h to about 275 mg/h. Exemplary rates of infusion can achieve a desired therapeutic dose of, for example, about 0.5 mg/m$^2$/day to about 10 mg/m$^2$/day, including about 1 mg/m$^2$/day to about 9 mg/m$^2$/day, about 2 mg/m$^2$/day to about 8 mg/m$^2$/day, about 3 mg/m$^2$/day to about 7 mg/m$^2$/day, about 4 mg/m$^2$/day to about 6 mg/m$^2$/day, about 4.5 mg/m$^2$/day to about 5.5 mg/m$^2$/day. Administration (e.g, by infusion) can be repeated over a desired period, e.g., repeated over a period of about 1 day to about 5 days or once every several days, for example, about five days, over about 1 month, about 2 months, etc. It also can be administered prior, at the time of, or after other therapeutic interventions, such as surgical intervention to remove cancerous cells. The anti-c-Met antibody can also be administered as part of a combination therapy, in which at least one of an immunotherapy, a cancer chemotherapy or a radiation therapy is administered to the subject (as described in greater detail below).

Disposition of the anti-c-Met antibody and its corresponding biological activity within a subject is typically gauged against the fraction of anti-c-Met antibody present at a target of interest. For example, a anti-c-Met antibody once administered can accumulate with a glycoconjugate or other biological target that concentrates the material in cancer cells and cancerous tissue. Thus dosing regimens in which the anti-c-Met antibody is administered so as to accumulate in a target of interest over time can be part of a strategy to allow for lower individual doses. This can also mean that, for example, the dose of anti-c-Met antibody that are cleared more slowly in vivo can be lowered relative to the effective concentration calculated from in vitro assays (e.g., effective amount in vitro approximates mM concentration, versus less than mM concentrations in vivo).

As an example, the effective amount of a dose or dosing regimen can be gauged from the $IC_{50}$ of a given anti-c-Met antibody for inhibiting cell migration. By "$IC_{50}$" is intended the concentration of a drug required for 50% inhibition in vitro. Alternatively, the effective amount can be gauged from the $EC_{50}$ of a given anti-c-Met antibody concentration. By "$EC_{50}$" is intended the plasma concentration required for obtaining 50% of a maximum effect in vivo. In related embodiments, dosage may also be determined based on $ED_{50}$ (effective dosage).

In general, with respect to the anti-c-Met antibody of the present disclosure, an effective amount is usually not more than 200× the calculated $IC_{50}$. Typically, the amount of an anti-c-Met antibody that is administered is less than about 200×, less than about 150×, less then about 100× and many embodiments less than about 75×, less than about 60×, 50×, 45×, 40×, 35×, 30×, 25×, 20×, 15×, 10× and even less than about 8× or 2× than the calculated $IC_{50}$. In one embodiment, the effective amount is about 1× to 50× of the calculated $IC_{50}$, and sometimes about 2× to 40×, about 3× to 30× or about 4× to 20× of the calculated $IC_{50}$. In other embodiments, the effective amount is the same as the calculated $IC_{50}$, and in certain embodiments the effective amount is an amount that is more than the calculated $IC_{50}$.

An effect amount may not be more than 100× the calculated $EC_{50}$. For instance, the amount of anti-c-Met antibody that is administered is less than about 100×, less than about 50×, less than about 40×, 35×, 30×, or 25× and many embodiments less than about 20×, less than about 15× and even less than about 10×, 9×, 8×, 7×, 6×, 5×, 4×, 3×, 2× or 1× than the calculated $EC_{50}$. The effective amount may be about 1× to 30× of the calculated $EC_{50}$, and sometimes about 1× to 20×, or about 1× to 10× of the calculated $EC_{50}$. The effective amount may also be the same as the calculated $EC_{50}$ or more than the calculated $EC_{50}$. The $IC_{50}$ can be calculated by inhibiting cell migration/invasion in vitro. The procedure can be carry out by methods known in the art or as described in the examples below.

Effective amounts of dose and/or dose regimen can readily be determined empirically from assays, from safety and escalation and dose range trials, individual clinician-patient relationships, as well as in vitro and in vivo assays.

Diagnostic Methods

The present disclosure provides a method of detecting c-Met (e.g. full-length or fragment) in a biological sample in a subject or in a sample isolated from a subject. The methods are useful to both diagnostic and prognostic purposes. A subject method generally involves contacting a sample containing a cell with an antibody of the present disclosure; and detecting binding of the antibody to a cell in the sample. The cell can be in vitro, where the cell is in a biological sample obtained from a subject suspected for having cancer cells, a subject undergoing cancer treatment, or a subject being tested for susceptibility to treatment. The cell can be in vivo, e.g., the cell is in a subject suspected for having cancer cells, a subject undergoing treatment, or a subject being tested for susceptibility to treatment.

Antibodies can be used to detect cells expressing c-Met in a biological sample of a subject having or suspected of having cancerous cells via immunodiagnostic techniques. Such diagnostics can be useful to identify patients amenable to the therapies disclosed later below, and/or to monitor response to therapy.

Suitable immunodiagnostic techniques include, but are not necessarily limited to, both in vitro and in vivo (imaging)

methods. For example, anti-c-Met antibodies can be detectably labeled, administered to a subject suspected of having a cancer characterized by cell surface expression of c-Met, and bound detectably labeled antibody detected using imaging methods available in the art.

The phrase "in vivo imaging" as used herein refers to methods of detecting the presence of an antibody (e.g. detectably labeled clone 21) in whole, live mammal. Optically detectable proteins such as fluorescent antibodies and luciferases-conjugated antibodies may be detected by in vivo imaging. In vivo imaging of fluorescent proteins in live animals is described in, e.g., Hoffman, *Cell Death and Differentiation* 2002, 9:786-789. In vivo imaging may be used to provide 2-D as well as 3-D images of a mammal. Charge-coupled device cameras, CMOS, or 3D tomographers may used to carry out in vivo imaging. For example, Burdette J E *Journal of Mol. Endocrin.*, 40: 253-261, 2008, reviews utilizing computed tomography, magnetic resonance imaging, ultrasonography, positron emission tomography, single-photon emission computed tomography (SPECT), etc. The information from many in vivo imaging methods as those described above can provide information on cancer cells in the subject.

Where the methods are in vitro, the biological sample can be any sample in which a cancer cell may be present, including but not limited to, blood samples (including whole blood, serum, etc.), tissues, whole cells (e.g., intact cells), and tissue or cell extracts. For example, the assay can involve detection of c-Met on live cells or cells in a histological tissue sample.

Particularly, detection can be assessed on an extracellular surface of a living cell. For example, the tissue sample may be fixed (e.g., by formalin treatment) and may be provided embedded in a support (e.g., in paraffin) or frozen unfixed tissue.

Assays can take a wide variety of forms, such as competition, direct reaction, or sandwich type assays. Examples of assays include Western blots; agglutination tests; enzyme-labeled and mediated immunoassays, such as enzyme-linked immunosorbent assays (ELISAs); biotin/avidin type assays; radioimmunoassays; immunoelectrophoresis; immunoprecipitation, and the like. The reactions generally include detectable labels conjugated to the antibody. Labels include those that are fluorescent, chemiluminescent, radioactive, enzymatic and/or dye molecules, or other methods for detecting the formation of a complex between antigen in the sample and the antibody or antibodies reacted therewith.

Where a solid support is used, the solid support is usually first reacted with a solid phase component under suitable binding conditions such that the antibody is sufficiently immobilized to the support. Sometimes, immobilization to the support can be enhanced by first coupling the antibody to a protein with better binding properties, or that provides for immobilization of the antibody on the support with out significant loss of antibody binding activity or specificity. Suitable coupling proteins include, but are not limited to, macromolecules such as serum albumins including bovine serum albumin (BSA), keyhole limpet hemocyanin, immunoglobulin molecules, thyroglobulin, ovalbumin, and other proteins well known to those skilled in the art. Other molecules that can be used to bind antibodies to a support include polysaccharides, polylactic acids, polyglycolic acids, polymeric amino acids, amino acid copolymers, and the like, with the proviso that the molecule used to immobilize the antibody does not adversely impact the ability of the antibody to specifically bind antigen. Such molecules and methods of coupling these molecules to the antibodies, are well known to those of ordinary skill in the art.

An ELISA method can be used, in which the wells of a microtiter plate are coated with a subject antibody. A biological sample containing or suspected of containing c-Met, is then added to the coated wells. After a period of incubation sufficient to allow antibody binding, the plate(s) can be washed to remove unbound moieties and a detectably labeled secondary binding molecule added. The secondary binding molecule is allowed to react with any captured antigen, the plate washed and the presence or absence of the secondary binding molecule detected using methods well known in the art.

Where desired, the presence or absence of bound c-Met from a biological sample can be readily detected using a secondary binder comprising an antibody directed against the antibody ligands. For example, a number of anti-bovine immunoglobulin (Ig) molecules are known in the art which can be readily conjugated to a detectable enzyme label, such as horseradish peroxidase, alkaline phosphatase or urease, using methods known to those of skill in the art. An appropriate enzyme substrate is then used to generate a detectable signal. In other related embodiments, competitive-type ELISA techniques can be practiced using methods known to those skilled in the art.

Assays can also be conducted in solution, such that the antibodies and the antigens form complexes under precipitating conditions. An antibody-coated particle can be contacted under suitable binding conditions with a biological sample suspected of containing the target antigen to provide for formation of particle-antibody-antigen complex aggregates which can be precipitated and separated from the sample using washing and/or centrifugation. The reaction mixture can be analyzed to determine the presence or absence of antibody-antigen complexes using any of a number of standard methods, such as those immunodiagnostic methods described above.

Alternatively, assays for cellular uptake in live cells can be another diagnostic technique to positively identify cancerous cells. Since the subject antibodies are specifically internalized by cells expressing c-Met, the cells can be allowed for internalization of the antibodies and any antibodies that are not internalized be washed away (e.g. acid wash). The internalized antibodies may be detected via its label as contained with the cells (e.g. FACS, spectrometer, radioisotope counter, etc.).

The diagnostic assays described herein can be used to determine whether a subject has a cancer that is more or less amenable to therapy using antibody-based therapy, as well as monitor the progress of treatment in a subject. It also may be used to assess the course of other combination therapies. Thus, the diagnostic assays can inform selection of therapy and treatment regimen by a clinician.

The above-described assay reagents, including the antibodies of the present disclosure, can be provided in kits, with suitable instructions and other necessary reagents, in order to conduct immunoassays as described above. The kit can also contain, depending on the particular immunoassay used, suitable labels and other packaged reagents and materials (i.e. wash buffers and the like). Standard immunoassays, such as those described above, can be conducted using these kits.

Kits and Systems

Also provided are kits and systems that find use in practicing the methods, as described above. For example, kits and systems may include one or more of the compositions described herein, such as an anti-c-Met antibody (e.g. clone 20 or clone 21), a nucleic acid encoding the same (especially a nucleic acid encoding a CDR of a heavy and/or light chain of any subject antibodies described above), or a cell containing the same. Other optional components of the kit include: buffers, etc., for administering the subject antibody, and/or for performing a diagnostic assay. The recombinant nucleic acids of the kit may also have restrictions sites, multiple cloning sites, primer sites, etc to facilitate their ligation to constant regions of nucleic acids. The various components of the kit may be present in separate containers or certain compatible components may be precombined into a single container, as desired.

The kits and systems for practicing the methods may include one or more pharmaceutical formulations that include the antibody compositions described herein. As such, the kits may include a single pharmaceutical composition present as one or more unit dosages. The kits may also include two or more separate pharmaceutical compositions.

In addition to the above components, the kits may further include instructions for practicing the methods. These instructions may be present in the kits in a variety of forms, one or more of which may be present in or on the kit. One form in which these instructions may be present is as printed information on a suitable medium or substrate, e.g., a piece or pieces of paper on which the information is printed, in or on the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means may be present in the kits.

A kit may be provided for use in treating a host suffering from a cellular proliferative disease. This kit includes a pharmaceutical composition comprising antibody specific for c-Met, and instructions for the effective use of the pharmaceutical composition in a method of treating a host suffering from a cancerous condition by inhibiting the growth of a cancer cell in a subject. Such instructions may include not only the appropriate handling properties, dosing regiment and method of administration, and the like, but can further include instructions to optionally screen the subject for a c-Met-associated disease. This aspect can assist the practitioner of the kit in gauging the potential responsiveness of the subject to treatment with an antibody of the present disclosure, including timing and duration of treatment relative to the type and growth stage of the cancer. Thus in another embodiment, the kit may further include an antibody or other reagent for detecting an epitope of c-Met on an extracellularly accessible surface of a cancer cell. In another embodiment, the kit includes antibody that comprises a conjugate with a detectable label, such as a fluorophore.

The term "system" as employed herein refers to a collection of antibodies described herein and one or more second therapeutic agents, present in single or disparate compositions that are brought together for the purpose of practicing the methods. For example, separately obtained antibody specific to c-Met and chemotherapy dosage forms brought together and coadministered to a subject are a system according to the present disclosure.

The following examples are put forth so as to provide those of ordinary skill in the art with a complete disclosure and description of how to make and use the subject invention, and are not intended to limit the scope of what is regarded as the invention.

Experimental

Methods

Cell Lines and Culture.

PC3 (prostate cancer), human lung cancer cell lines including H1993, H460, H441, A549 and CL1-5 were grown in RPMI 1640 containing 10% FBS (Invitrogen) at 37° C. under a humidified atmosphere containing 5% $CO_2$. SAS (oral cancer), HCT116 (colon cancer), Mahlavu (liver cancer), NPC-TW04 (nasopharyngeal cancer) (Lee et al. (2004) *Cancer Res* 64:8002-8008), PaCa (pancreatic cancer), U2OS (osteosarcoma) and 293T were grown on DMEM with 10% FBS. A498 (renal cell carcinoma) was cultured in MEM. MDA-MB231 (breast cancer) was cultured in F12 medium mixed with 50% DMEM under 10% $CO_2$ atmosphere. CL1-5 was established by Chu et al. (1997) *Am J Respir Cell Mol Biol* 17:353-360. Mahlavu was a gift from Dr. Hsiao M (GRC, Academia Sinica, Taiwan). Other cell lines were obtained from the American Type Culture Collection. Preparation of human umbilical vein endothelial cells (HUVECs) and human normal nasal mucosal (NNM) cells have been described in previous studies (Lee et al. (2007) *Cancer Res* 67:10958-10965; Lee et al. (2004) *Cancer Res* 64:8002-8008).

Construction of phage-displayed human naïve scFv library. Briefly, cDNA was synthesized from mRNA mixture of seven individual samples of human splenocyte tissue using Superscript III reverse transcriptase (Invitrogen) by oligo dT primers. $V_H$ and $V_L$ genes were amplified by PCR using PfuUltra polymerase (EMD Biosciences) with specific primers (Marks et al., 1991). The PCR products were isolated and purified from agarose gel using a nuclei acid purification kit (Qiagene). The $V_H$ and $V_L$ gene encoding regions were assembled by DNA fragment encoding (SEQ ID NO:2) $(GGGGS)_3$ amino acid residues by PCR using primers containing specific restriction enzyme site at the 5'(SfiI) and 3' (NotI) end, respectively. The assembled products were digested with restriction enzyme by SfiI and NotI (NEB) followed by ligating into pCANTAB-5E phagemid vector (GE Healthcare). The human scFv gene-containing pCANTAB-5E vectors were electroporated into competent TG1 *E-coli* cells. After electroporation, TG1 *E-coli* cells were recovered and incubation continued in 2YT medium (BD) containing 100 µg/ml ampicillin and 2% glucose (2YT-AG). TG1 cells were rescued by M13KO7 phage, and then phage particles displaying scFv were produced in the culture medium.

Selection of Phage-Displayed Anti-c-Met scFv by Library Biopanning.

Selection of phages displaying specific anti-c-Met scFv was performed by protein G dynabeads (Invitrogen). c-Met-Fc recombinant protein (R&D) was incubated with protein G dynabeads at room temperature (RT) for 1 hr. The scFv library ($2 \times 10^9$ members) was subtracted non-specific binding in protein G dynabeads and subsequently incubated with c-Met-Fc immobilized dynabeads for 1 hr at 4° C. Unbound phages were removed by washing 4 times with PBST. The phages that bound to c-Met-Fc were recovered by infection with *E. coli* TG1 cells at 37° C. for 30 min. Part of the infected cells were serial diluted to determine titer, and the others were rescued by M13KO7 helper phage (NEB). After determination of rescued phages titer, the next round of biopanning was performed. In the forth and fifth round of biopanning the phage clones were randomly selected to culture for ELISA screening.

Evaluation of the Binding Specificity of the Selected Phage Clone to c-Met-Overexpressing 293T Cells.

For immunofluorescence staining assay, 293T cells were grown on coverslips to 80% confluence. Transfection of the cells with pEF-c-Met expression vector was performed using Lipofectamin 2000 (Invitrogen) according to manufacturer's instructions. At 48 hrs post-transfection, the cells were incubated with the selected anti-c-Met phage or control phage, by $1 \times 10^{10}$ phage titer for 30 min at 4° C. After the cells were washed twice with PBS, they were fixed by 4% paraformaldehyde, permeabilized with 0.1% TritonX-100 and blocked with 3% BSA. The cells were probed with rabbit anti-myc antibody (Sigma-Aldrich) and mouse anti-M13 phage antibody, followed by staining with Rhodamine-labeled goat anti-rabbit IgG and FITC-labeled anti-mouse IgG, respectively. The nuclei were stained with DAPI. The fluorescence images were captured by inverted fluorescence microscope (Axiovert 200M, Zeiss).

For flow cytometry analysis, 293T cells were grown to 80% confluence and transfected with pEF-c-Met expression vector as described above. After 48 hrs, the transfected cells were harvested by 0.05% Trypsin-EDTA, and incubated with the selected phage or control phage by $1 \times 10^{10}$ phage titer in FACS buffer (PBS containing 1% fetal bovine serum) for 1 hr at 4° C. After we washed the cells with FACS buffer, we incubated them with mouse anti-M13 phage Ab for 1 hr at 4° C. followed by incubation of R-phycoerythrin-conjugated goat anti-mouse IgG (Jackson ImmunoResearch) for 30 min at 4° C. Analysis was performed using FACSCantoII (BD) and emission fluorescence intensity was measured by FACS-Diva software (BD) to quantitatively compare their binding affinities Expression and Purification of Soluble scFv.

Anti-c-Met scFv phage clone 1, 20 and 21 were infected to E-coli strain HB2151, individually, and periplasmic extracts of bacteria were prepared. Soluble scFv was purified in periplasmic extracts by Protein L agarose column (Thermo Scientific) according to manufacturer's instructions. Purified scFvs were completely dialyzed with PBS and analyzed by reducing SDS-PAGE followed by coomassie blue staining and Western blot analysis by probing with anti-E tag Ab (GE Healthcare).

Construction of Mammalian Expression Vector Encoding Human c-Met Gene.

The entire human c-Met cDNA (NM_001127500.1) was synthesized from total RNA of HepG2 cells using Superscript III reverse transcriptase by specific primers and then used as a PCR template. The DNA encoding full-length c-Met was amplified by PCR with PfuUltra enzyme and ligated in frame with myc-tag epitope pEF vector (Invitrogen) to generate pEF-c-Met-myc. DNA fragments encoding amino acid residues 1 to 932 and 1 to 567 of c-Met were amplified by PCR and cloned to pEF vector to create pEF-c-Met$_{932}$ and pEF-c-Met$_{567}$, respectively. The coding region of human IgG$_1$ Fc was obtained from human splenocyte cDNA library followed by cloning in frame to carboxyl termini of c-Met$_{932}$ and c-Met$_{567}$ to generate pEF-c-Met$_{932}$-Fc and pEF-c-Met$_{567}$-Fc, respectively.

Production and Purification of c-Met-Truncated Recombinant Protein.

c-Met$_{932}$-Fc and c-Met$_{567}$-Fc fusion protein were prepared from culture supernatants of 293T cells that had been transiently transfected using Lipofectamin 2000 with pEF-c-Met$_{932}$-Fc or c-Met$_{567}$-Fc, respectively. At 72 hrs post-transfection, filtered supernatants were applied to 1 ml protein G agarose column (GE healthcare). After being washing with PBS, bound proteins were eluted with 0.1 M glycine-HCl pH 2.8 followed by neutralization with 1 M Tris-HCl pH 9.1. The eluent was fully dialyzed with PBS and concentrated using Amicon Ultra-4 Centrifugal filter (cut-off 10 kDa; Millipore).

Internalization of Anti-c-Met scFv Viewed by Confocal Microscopy.

H1993, H460, and c-Met-knockdown H460 cells were seeded on coverslips and grown to 80% confluence. The cells were incubated with anti-c-Met scFv S1 or S20 for 30 minutes at 4° C. and 37° C. After being washed twice with PBS, the cells were fixed by 4% paraformaldehyde and blocked by adding 3% BSA. The cells were stained by anti-Flag antibody (Sigma-Aldrich) and then probed with FITC-labeled goat anti-mouse IgG (Jackson ImmunoResearch) and DAPI (Invitrogen). All fluorescence images were obtained by confocal microscopy (TCS-SP5, Leica).

Construction of Prokaryotic Expression Vector for Production of Anti-c-Met scFv20-Cys (Ms20).

The prokaryotic expression vector, pFHC, was generated by removing E tag and pIII DNA fragment via NotI-EcoRI enzyme digestion from pCANTAB-5E and inserting the synthesized DNA fragment that encoded a FLAG tag, hexahistidine and a cysteine residue through the NotI-EcoRI site. The anti-c-Met S20 gene digested from pCANTAB-5E-S20 was ligated to pFHC vector via the NcoI-NotI site. The constructed vector was transformed into E. coli BL21 (Novagen) to express the scFv containing hexahistidine and a cysteine at the carboxyl termini.

Expression and Purification of Anti-c-Met scFv20-Cys (Ms20).

A single colony of E. coli BL21 was inoculated in Terrific Broth (TB; MDBio, Taiwan) containing 100 µg/ml ampicillin (TB-A) and incubated overnight at 30° C. A 1/50 volume dilution of overnight culture was grown in fresh 2.5 liter TB-A at 30° C. until an OD600 of 0.5 was reached. Induction was initiated by adding IPTG to a final concentration of 0.4 mM and by directly dissolving 0.4 M sucrose in TB-A. The cultivation was continued for 16 hr at 30° C. with shaking at 250 rpm.

The supernatant was removed by centrifugation at 20,000×g for 30 min, and then the bacteria pellet was resuspended in cold 200 ml TES buffer (10 mM Tris, 20% sucrose and 1 mM EDTA pH 8.0; EMD Biosciences) and incubated at 4° C. for 1 hr with gentle stirring. The osmotic shock fraction was collected by centrifugation at 22,000×g for 30 min. The periplasmic extract was obtained by incubating the pellet in ice-cold 5 mM MgSO$_4$ for 1 hr with gentle shaking.

Osmotic shock fraction and periplasmic extract were combined for maximal recovery of Ms20, and to the combined sample NaCl was added to a final concentration of 0.5 M and imidazol to final concentration of 0.5 mM. The 5 ml of Ni$^+$-NTA sepharose column (GE Healthcare) was equilibrated with 15 ml binding buffer (20 mM Tris, 0.5 M NaCl and 5 mM Imidazol pH 7.9), followed by loading sample. The bound Ms20 was eluted with elution buffer (20 mM Tris, 0.5 M NaCl and 1 M Imidazol pH 7.9). The eluent was thoroughly dialyzed against PBS at 4° C. for two changes. After dialysis, the sample was re-purified by protein A agarose column (2 ml) (GE Healthcare). The re-purified Ms20 was dialyzed against HEPES buffer (20 mM HEPES, 150 mM NaCl and 1 mM EDTA, pH 7.0) for two changes, and then concentrated by 10 kDa-cutoffs tube (Amicon Ultra, Millipore).

Measurement of Binding Kinetics.

The affinity and kinetics of anti-c-Met scFv were measured by SRP in BIAcore X (GE healthcare). In BIAcore flowcell, 30 µg/ml of c-Met$_{932}$-Fc protein was coupled to EDC- and NHS-activated CM5 sensor chip followed by blocking with ethanolamine according to manufacturer's directions. Associated and dissociated phases were monitored for 3 and 5 min, respectively, under continuous flow of 30 µl/min using scFv concentrations ranging 5 to 200 nM. Regeneration was performed by injection of regenerate buffer (0.2 M NaCl, 10 mM glycine, pH 2.7). To determine binding constants, the sensorgrams were fit globally to a sample 1:1 interaction model using BIAevaluation software (GE healthcare).

Competition Binding Assay.

To monitor inhibition effect of scFv, we coated the c-Met$_{932}$-Fc protein on a 96-well plate and blocked nonspecific binder with 3% BSA in PBS. 1 nM human HGF (R&D) plus varying concentrations of anti-c-Met scFv or normal mouse IgG were applied to the wells. The amount of HGF bound to c-Met was determined using goat anti-human HGF (R&D), following incubation of HRP-labeled mouse anti-goat IgG (Jackson ImmunoResearch) and OPD substrate (Sigma) plus $H_2O_2$. The absorbance was measured with 490 nm using a microplate reader. Inhibition percentage was calculated by the following equation: [(the absorbance of HGF bound without competitor)−(the absorbance of HGF bound with competitor)]/(the absorbance of HGF bound without competitor)×100%.

Construction of Ms20-Targeting Liposomal Doxorubicin (Ms20-LD).

To ensure the purified Ms20 had reduced thiol group for conjugation, we treated 2 mM TCEP (tris(2-carboxyethyl) phosphine; Sigma-Aldrich) to reduce intermolecular disulfide bonds of Ms20 at room temperature for 2 hr under $N_2$ atmosphere. The reduced Ms20 was desalted by HiTrap G-25 column (GE healthcare) eluted by HEPES buffer. Incorporation of maleimide-carboxyl polyethylene glycol ($M_r$ 2,000)-derived distearoylphosphatidylethanolamine (maleimide-PEG-DSPE; NOF Corporation, Japan) into pegylated liposomal doxorubicin (Lee et al., 2004; Lo et al., 2008) was described as below. Maleimide-PEG-DSPE was dissolved in HEPES buffer and added to LD at 0.5 mole % of the liposome phospholipids, and the mixture was incubated at 60° C. for 1 hr with gentle shaking. The reduced Ms20 was incubated with maleimide-PEG-DSPE-inserting LD for conjugation at 4° C. overnight to generate about 60 molecules of Ms20 in one liposome. After using 2-mercaptoethanol (2 mM of final concentration) to inactive all unreactive maleimide groups, we used Sepharose 4B (GE healthcare) gel filtration chromatography to remove released free drug, unconjugated scFv, and unincorporated conjugates. Doxorubicin concentrations in the fractions of eluent were measured using a spectrofluorometer (Spectra Max M5, Molecular Devices) at $\lambda_{Ex/Em}$=485/590 nm. The Ms20-LD fractions were separated by reducing SDS-PAGE followed by staining with sliver nitrate conjugation efficiency for estimation of conjugation efficiency.

Identification of Ms20-LD Binding to Human Lung Cancer Cells.

The cells were grown on a 12-well plate to 90% confluency. The plated cells were incubated with serial dilution of LD or Ms20-LD (0.625-10 µg/ml doxorubicin) at 4° C. for 1 hr. After incubation, the cells were washed with PBS, and lysed with 200 µl 1% Triton X-100. For extraction of doxorubicin, 300 µl IPA (0.75 N HCl in isopropanol) was added to the lysate and shaken for 30 min. After the lysates were centrifuged at 12,000 rpm for 5 min, the supernants were measured for doxorubicin by spectrofluorometer at $\lambda_{Ex/Em}$=485/590 nm. The concentration of doxorubicin was calculated by intrapolation using a standard curve.

Uptake of Ms20-LD by Human Cancer Cells.

The tumor cells were grown on a 12-well plate to 90% confluency, 2.5 µg/ml Ms20-LD or LD in complete culture medium was added and incubation was continued at 37° C. for the indicated times. After the cells were washed with PBS, Ms20-LD and LD on cell surface was removed by 0.1 M Glycine pH 2.8 for 10 min. The amounts of doxorubicin uptake by cells were detected as described above.

Confocal Microscopy Analysis for Cellular Uptake of Ms20-LD.

H1993 cells were grown on coverslips to subconfluency. The cells were incubated in complete culture medium containing 2.5 µg/ml of Ms20-LD or LD at 37° C. for various time periods. After being washed twice with PBS, the cells were fixed with 4% paraformaldehyde and blocked by adding 3% BSA. Cell membrane and nucleus were stained with Alexa Fluor 647-conjugated wheat germ agglutinin (Invitrogen) and DAPI (Invitrogen), respectively. Intracellular doxorubicin was detected with fluorescence at $\lambda_{Ex/Em}$=485/590 nm. All fluorescence images were captured by laser scanning confocal microscopy (TCS-SP5, Leica) and analyzed with LAS AF software (Leica).

Cell Viability Assay.

Cells were seeded in 96-well plates at 3,000 per well and incubated with MS20-LD or LD in culture medium (10% FBS) at varying concentrations (0-20 µg/ml) at 37° C. for 24 hrs. After removal of the excess drug, the cells were washed once with PBS and incubation was continued with culture medium for 48 hrs at 37° C. The cell viability was detected by MTT (Invitrogen) assay. The cells were incubated with culture medium containing 0.1 mg/ml MTT at 37° C. for 2.5 hrs. The formazan crystals were subsequently dissolved in DMSO (Sigma-Aldrich), and absorbance was measured with 540 nm using a microplate reader (Model 680, BioRad). Each assay was repeated three times. The data was presented as the percent of viable cells compared with that of untreated control cells.

In Vitro Cell Apoptosis Study.

H1993 cells were seeded on a 24-well plate, allowed to adhere overnight, and then cultured with 2.5 µg/ml Ms20-LD or LD in RPMI 1640 containing 10% FBS, individually. After incubation with the drug for 24, 48, and 72 hrs, the cells were harvested in lysis buffer (Cell Signaling) and subjected to Western blot analysis. The following antibodies were used: rabbit anti-cleaved caspase 9 (Asp315), rabbit anti-cleaved caspase 3 (Asp175), rabbit anti-PARP (all purchased from Cell Signaling), and mouse anti-α-tubulin (Sigma-Aldrich). Chemiluminescence signal was detected using BioSpectrum 600 imaging system (UVP) and quantitated with VisionWorksLS software (UVP).

Synthesis of scFv-Conjugated Quantum Dots (QD).

Qdot 705 and Qdot 800 ITK amino PEG quantum dots (Invitrogen) were used in the studies for in vitro cell binding and in vivo imaging, respectively. The procedures for synthesis of ligand-conjugated QD were modified from a previous report (Cai and Chen (2008) *Nat Protoc* 3:89-96). Briefly, QD were conjugated with sulfo-SMCC (Sulfosuccinimidyl-4-(N-maleimidomethyl) cyclohexane-1-carboxylate; Pierce) to generate a maleimide-activated surface on QD, and free sulfo-SMCC was removed by NAP-10 desalting column (GE healthcare). Ms20 was reduced by TCEP to yield activated thiol group in the carboxyl terminus, and subsequently incubated with the maleimide-functionalized QD at 4° C. overnight. Ms20-conjugated QD was purified using sepharose 4B gel filtration chromatography eluted with HEPES buffer. The concentration of QD was examined with spectrofluorometer and calculated by intrapolation using a standard curve.

In Vivo Fluorescence Imaging of Human Tumor Xenografts.

Six 12-week old SCID male mice were subcutaneously implanted with $2 \times 10^6$ H1993 cells. When the size of tumors reached around 300 mm³, the mice were randomly divided into two groups (3 mice in each group) and intravenously injected with 400 pmole of Ms20-QD or QD, respectively. While mice were under isofluoran anesthetization, fluorescence images were captured using a Xenogen IVIS 200 imaging system (Excitation: 525/50 nm; Emission: 832/65 nm) at indicated times. At the end of imaging sessions, mice were sacrificed by cervical dislocation. The organs and tumors were excised from the mice and subjected to fluorescence imaging. To quantitatively compare tumor accumulation of Ms20-QD with accumulation of QD, the fluorescence intensity was calculated by subtracting background using Living image software (Xenogen).

Animal Model for In Vivo Phage Targeting Assay.

Six SCID mice (6-week old) were injected subcutaneously with $5\times10^6$ lung cancer cells. When the tumors reached about 300 mm$^3$, the mice were randomly separated into two groups (3 mice in each group) and intravenously injected with $2\times10^9$ colony forming unit (cfu) of anti-c-Met scFv phage clone 20 or control phage. After perfusion with 50 ml PBS, the organs and tumor tissue were removed, washed with cold PBS and weighed. The phages that bound to tumor tissues were recovered by growing TG1 and titer for eluted phages were measured.

The tissue distribution of targeting phages in human tumor-bearing mice was evaluated by immunohistochemistry using a Super Sensitive Polymer-HRP IHC Detection System (Bio-Genex). The paraffin-embedded tissue specimens were stained with mouse anti-M13 Ab followed by incubation with Super Enhancer reagent and polymer horseradish peroxidase-labeled anti-mouse IgG. After being washed with PBST (0.1% Tween 20 in PBS), the sections were immersed in 3,3'-diamino-benzidine (DAB) solution plus 0.01% $H_2O_2$ and washed with PBST. The tissue sections were counterstained by hematoxylin, mounted with 50% glycerol in PBS, and examined using upright microscopy (Axioplan 2 Imaging MOT, Zeiss). Animal care was in accordance with guidelines of Academia Sinica, Taipei, Taiwan.

Animal Model for Measurement of Antitumor Efficacy by scFv-Targeted Therapy.

SCID mice bearing H460-derived lung cancer xenografts (~75 mm$^3$) were intravenously injected in the tail vein with Ms20-LD, LD or equivalent volumes of PBS at a total doxorubicin dose of 4 mg/kg (1 mg/kg, once a week). Tumors were measured by caliper twice weekly and mice were observed routinely for weight loss as a symptom of drug toxicity. The tumor volumes were calculated according this formula: length×(width)$^2$×0.52.

Terminal Deoxynucleotidyl Transferase-Mediated dUTP Nick End Labeling (TUNEL) Assay.

The tumors were removed from treated mice and embedded with O.C.T Compound (Tissue-Tek) in liquid nitrogen. The frozen tumor tissue sections were prepared and treated with TUNEL reagents according to manufacturer's instructions (Roche Diagnostics) and counterstained by DAPI. Whole sections were scanned using TissueFAXS System microscopy (TissueGnostics). Reactivity of cells was quantified by MetaMorph software (Molecular Devices) by setting DAPI as master channel for identification of all cells.

Tumor vessel staining. The sections were prepared from the frozen tumor tissues. The sections were fixed with 1% paraformaldehyde, washed with PBS, and blocked in normal horse serum (Vector Laboratories) followed by incubation with rat anti-mouse CD31 (BD). After being washed with PBS containing 0.1% Tween 20, the sections were immersed with Alexa Fluor 594-conjugated anti-rat IgG (Invitrogen). The sections were scanned by TissueFAXS System microscopy, and the fluorescence images were analyzed by Meta-Morph.

Example 1

Identification of Phage-Displayed scFv that Binds to c-Met

To select a c-Met-binding scFv, phage-displayed human naïve scFv library containing $2\times10^9$ members was constructed. Dynabeads-binding phages were first removed from the library before selecting for c-Met-binding phages by c-Met-conjugated Dynabeads. After five rounds of affinity selection, the phage recovery of the fifth round had increased about 1000-fold that of the first round (FIG. 1, panel A). Fifty-nine phage clones were randomly selected and tested for c-Met binding by ELISA. Fourteen phage clones were found to have superior binding activity to c-Met-Fc protein ($A_{490}$>0.2). Control phage (Con-P) was used as a negative control. Sixteen clones that specifically bound to c-Met were identified, but not to VEGFR2 and BSA control protein (FIG. 1, panel 8). By sequencing all 16 individual clones, three unique anti-c-Met phage clones were identified (PC1, PC20, and PC21). See Table 1 below.

TABLE 1

Amino acid sequences of $V_H$ and $V_L$ domains of anti-c-Met scFvs $V_H$ domains

| | FW1 | CDR1 | FW2 | CDR2 |
|---|---|---|---|---|
| clone 1 | MAQVQLQQSGPGLVKPSQTLSLTCDISGDS (SEQ ID NO: 1) | VSSNSAAW (SEQ ID NO: 2) | NWIRQSPSRGLEWL (SEQ ID NO: 3) | GRTYYRSRWYNEYAVSVRG (SEQ ID NO: 4) |
| clone 20 | MAQVQLQQSGGKLVQPRGSLRLSCAASGFS (SEQ ID NO: 5) | LGSYAM (SEQ ID NO: 6) | SWVRQAPGKGLEWV (SEQ ID NO: 7) | STKDSDGTTYYADSVRG (SEQ ID NO: 8) |
| clone 21 | MAEVQLVESGPGLVKPSGTLSLKCDASAIS (SEQ ID NO: 9) | MDSNYWW (SEQ ID NO: 10) | SWLRQPPGKGLEWI (SEQ ID NO: 11) | GEISHSGSTDYNPSLKS (SEQ ID NO: 12) |
| | FW3 | CDR3 | FW4 | Family |
| clone 1 | RISINAETSKNQFSLQLNSVTPEDTAIYYCAR (SEQ ID NO: 13) | AGFCSGGNCYPGSED (SEQ ID NO: 14) | AFDLWGQGTMVTV (SEQ ID NO: 15) | $V_H$6 |
| clone 20 | RFTIARDNSKNTLYLQMNSLRAEDTAIYYCAR (SEQ ID NO: 16) | DFPGGPN (SEQ ID NO: 17) | AFDFWGQGTMVTV (SEQ ID NO: 18) | $V_H$3 |
| clone 21 | RATISIDKSKKQFFLRLKSVTAADTAVYYCA (SEQ ID NO: 19) | GLLSPLD (SEQ ID NO: 20) | AFDEWGQGTMVTV (SEQ ID NO: 21) | $V_H$4 |

$V_L$ domains

| | FW1 | CDR1 | FW2 | CDR2 |
|---|---|---|---|---|
| clone 1 | DVVMTQSPPSLS VSVGDRVTIT (SEQ ID NO: 22) | CRASQDITNDLN (SEQ ID NO: 23) | WYQQKPGKAPQLLIY (SEQ ID NO: 24) | HASELET (SEQ ID NO: 25) |
| clone 20 | DIVMTQSPATLSLSPGERATLS (SEQ ID NO: 26) | CRASQSITTYLV (SEQ ID NO: 27) CRASQRVATYL | WYQQKPGQAPRLLIY (SEQ ID NO: 28) | DASNRAT (SEQ ID NO: 29) |

TABLE 1-continued

Amino acid sequences of $V_H$ and $V_L$ domains of anti-c-Met scFvs

| clone 21 | DIQMTQSPSSLSASVGDRVTIT (SEQ ID NO: 30) | N (SEQ ID NO: 31) | WYQQKPGKAPNLLIY (SEQ ID NO: 32) | EASSLQS (SEQ ID NO: 33) |
|---|---|---|---|---|
| | FW3 | CDR3 | FW4 | Family |
| clone 1 | GVPSRFSGSGFGTDFTLTISSLQPADIATYYC (SEQ ID NO: 34) | QQYDDLPLT (SEQ ID NO: 35) | FGGGTKVEIKR (SEQ ID NO: 36) | $V_K1$ |
| clone 20 | GIPARFSGSGSGTDFTLTISSLEPEDFAVYFC (SEQ ID NO: 37) | QQRSDWPPT (SEQ ID NO: 38) | FGGGTKVEIKR (SEQ ID NO: 39) | $V_K3$ |
| clone 21 | GVPSRFSGRRSGTDFTLTISSLQPEDFATYYC (SEQ ID NO: 40) | QQSYNTPYT (SEQ ID NO: 41) | FGQGTRLEIKR (SEQ ID NO: 42) | $V_K1$ |

Complementarity-determining regions 1-3 (CDR1-3), and framework regions 1-4 (FW1-4) for both the $V_H$ and $V_L$ domains are shown in table above. The V domain families were aligned by VBASE2 database (www.vbase2.org).

Figure 8:
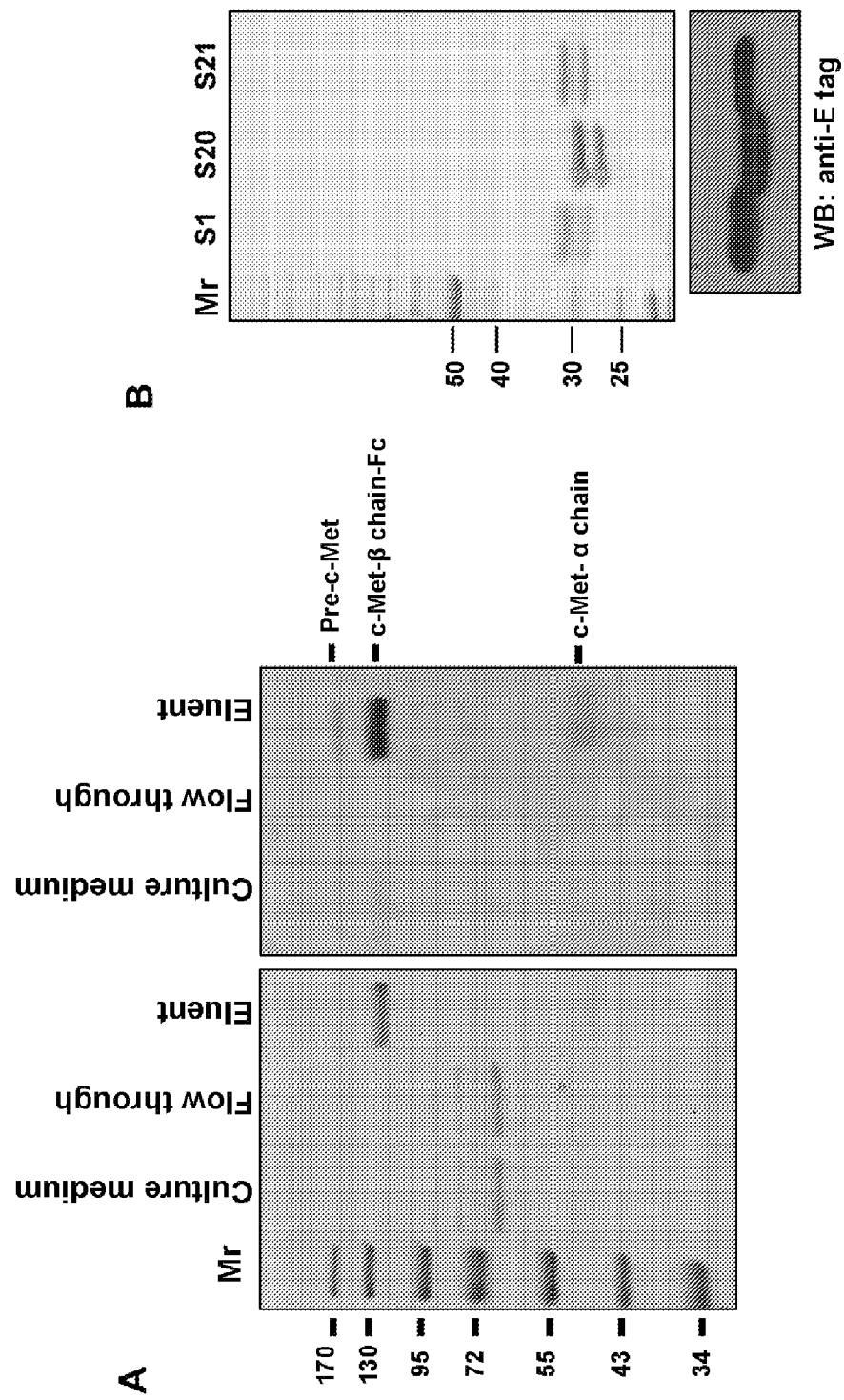
FIG. 8. Purification of soluble c-Met$_{932}$-Fc protein and anti-c-Met scFv. A, Comassie blue staining (left panel) and Western blot analysis using anti-c-Met polyclonal antibody (right panel). Lane 1, total culture media, lane 2, protein G column flow-through, and lane 3, purified soluble c-Met$_{932}$-Fc protein. B, soluble anti-c-Met scFvs were purified from periplasmic extract of phage-infected *E-coli* HB2151. Western blot analysis showed the soluble scFvs was recognized by anti-E tag antibody (lower panel).

To examine the specificity and binding affinity of the three phage clones, a comparative ELISA using the same phage titer was performed. The PC1 had a stronger c-Met binding affinity than either PC20 or PC21 (FIG. 1, panel C). The three clones were assessed for binding to cell-surface c-Met by flow cytometry and immunofluorescence assay using 293T cells ectopically expressing human c-Met. The phage particles were incubated with 293T cells overexpressing c-Met, following detection of phage particles and exogenous c-Met by anti-M13 and anti-myc antibodies, respectively. The representative images in FIG. 1, panel E illustrate anti-c-Met phages colocalized with c-Met-myc, which indicate their binding specificity for the cell expressed c-Met. All three clones bound to 293T cells with overexpressed c-Met, but not to 293T cells (FIG. 1, panels D and E). However, similarly, the binding ability of PC1 for cellular c-Met was higher than that of PC20 and PC21. Subsequently, to investigate the kinetic constants of anti-c-Met scFvs, c-Met$_{932}$-Fc recombinant protein was produced as well as soluble anti-c-Met scFvs named S1, S20, and S21, corresponding to PC1, PC20, and PC21, respectively Soluble c-Met$_{932}$-Fc protein was purified from culture media of ectopically c-Met$_{932}$-Fc-expressing 293T cells through protein G sepharose column (FIG. 8). Soluble anti-c-Met scFvs were purified from periplasmic extract of phage-infected *E-coli* HB2151 by protein L agarose chromatography, and then assessed by coomassie blue staining representing purified anti-c-Met scFv proteins (S1, S20 and S21) localized in vicinity of 30 kDa corresponding to protein weight marker (upper panel of FIG. 8, panel B).

Binding kinetic constants ($K_{on}$ and $K_{off}$) and affinity of each soluble scFv for c-Met$_{932}$-Fc protein were measured by Surface Plasmon Resonance (SPR). $K_d$ values of each soluble scFv for c-Met$_{932}$-Fc ranged from 6.82 to 14.9 nM. See Table 2 below.

TABLE 2

Kinetic constants and binding affinities of anti-c-Met scFvs

| scFv | $K_d$ (M) | $K_{on}$ (M$^{-1}$s$^{-1}$) | $K_{off}$ (s$^{-1}$) |
|---|---|---|---|
| clone 1 | $6.82 \times 10^{-9}$ | $2.15 \times 10^5$ | $1.34 \times 10^{-3}$ |
| clone 20 | $9.14 \times 10^{-9}$ | $1.06 \times 10^5$ | $0.97 \times 10^{-3}$ |
| clone 21 | $14.9 \times 10^{-9}$ | $2.61 \times 10^5$ | $3.89 \times 10^{-3}$ |

$K_{on}$ and $K_{off}$ were measured by SRP in a BIAcore using purified scFvs, and the $K_d$ was calculated by BIAevaluation software.

Example 2

Anti-c-Met scFvs Bound to Human Cancer and VEGF-Stimulated Endothelial Cells

Figure 9A:
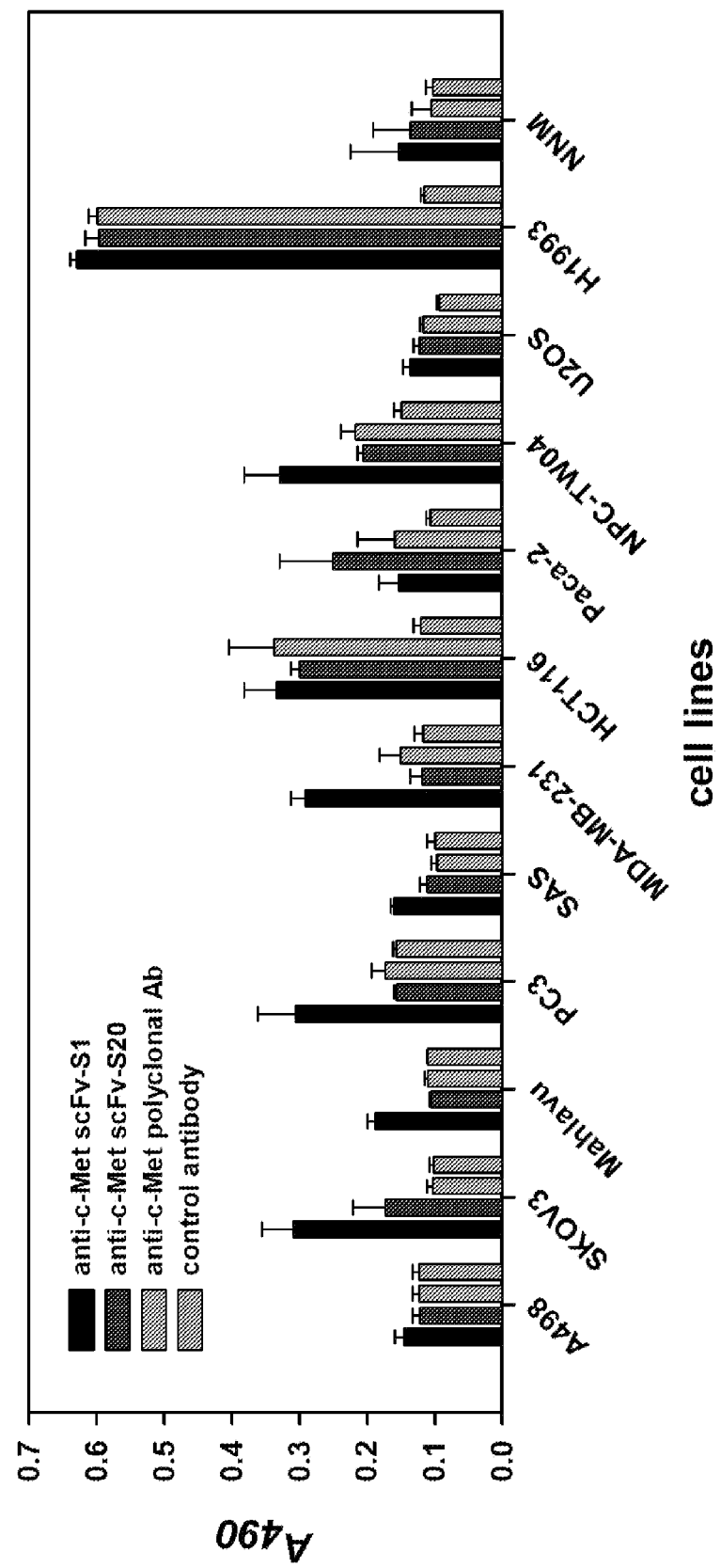
FIG. 9. Investigation of anti-c-Met scFvs binding to various human cancer cell lines and vascular endothelial cells (HUVECs). A, ELISA results from anti-c-Met scFv S1 or S2 against various human cancer cell lines B, the binding of anti-c-Met scFvs to HUVECs analyzed by flow cytometry.

The binding activities of anti-c-Met scFvs to endogenous c-Met were analyzed in cancer cells by ELISA (FIG. 9, panel A). Compared to the control antibody, both anti-c-Met S1 and S20 were found to bind to several types of human cancer cell lines, including SKOV3, Mahlavu, SAS, PC3, MDA-MB-231, HCT116, Paca-2, NPC-TW04, H1993 cells. However, the scFvs did not react with A498, U2OS, and NNM cells. Normal mouse IgG was used as a control antibody. FACS analysis was performed to verify that the Both anti-c-Met scFvs also bound VEGF-stimulated HUVECs. Anti-CD31 antibody and control scFv were used a positive and negative control, respectively (FIG. 9, panel B).

Figure 10:
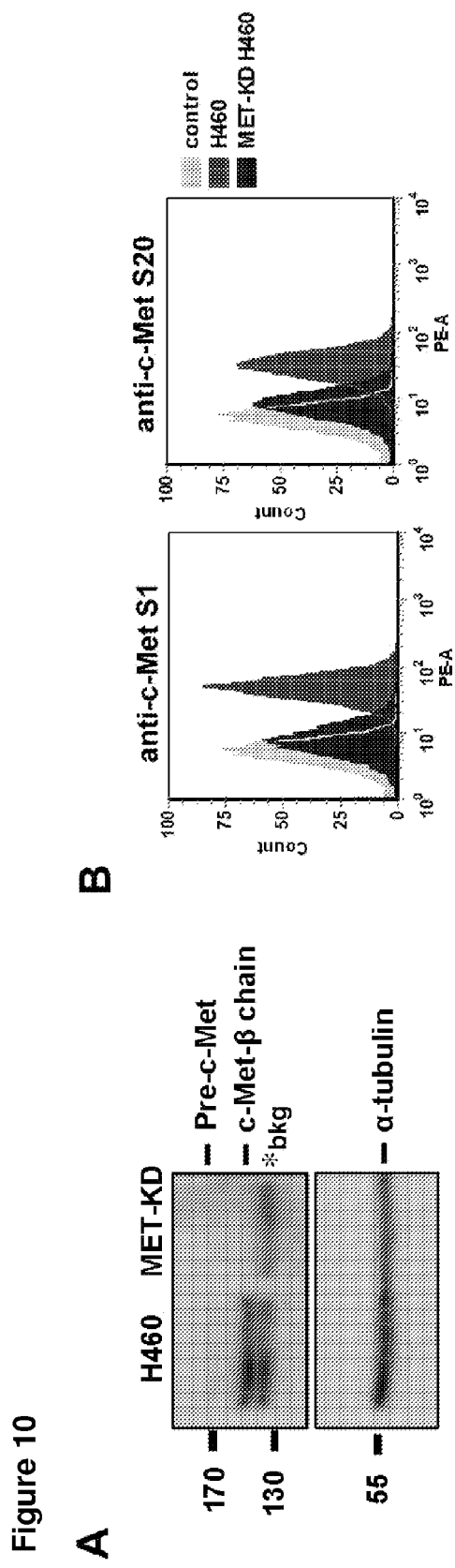
FIG. 10. Anti-c-Met scFvs specifically bound to endogenous c-Met on human lung cancer cells. A, Western blot analysis showed that down-regulation of c-Met in H460 cells (MET-KD H460 cells) by infection with the Lentivirus expressed c-Met shRNA. B, FACS analysis of anti-c-Met scFvs binding to c-Met wildtype and knockdown H460 cells.

To further confirm that the anti-c-Met scFv would bind specifically to endogenous c-Met on human cancer cells, H460 cells and c-Met knockdown H460 cells were stained with anti-c-Met scFv, either S1 or S20, and FACS analysis was carried out (FIG. 10, panel B). Both scFvs were able to bind H460 cells, but the binding activity of scFvs was dramatically decreased in c-Met knockdown H460 cells. β-tubulin served as a negative control and *bkg refers background signal in FIG. 10, panel A.

Example 3

Competition of HGF Binding to Cancer Cells by Anti-c-Met scFv

Figure 2:
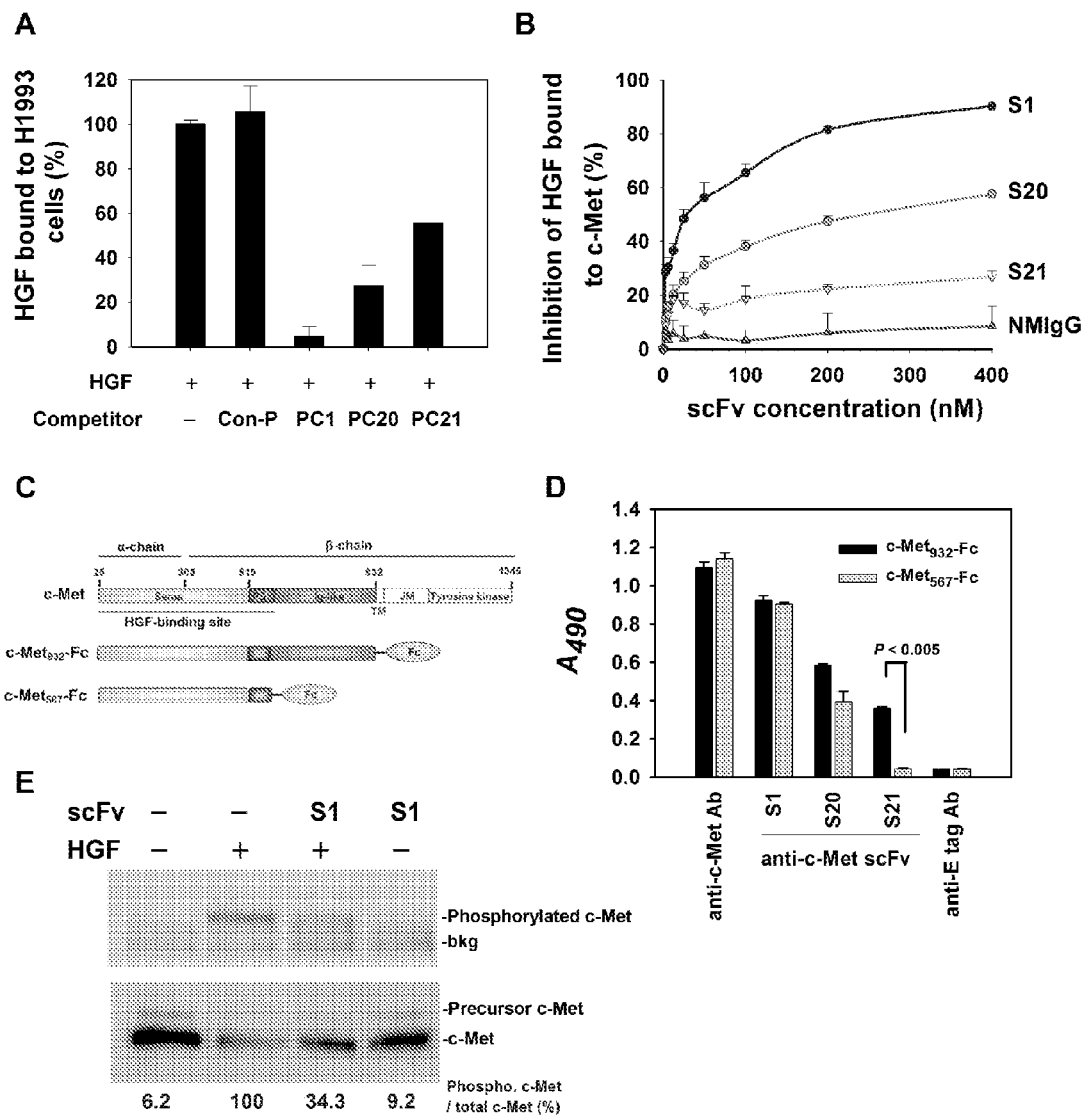
FIG. 2. Competition of HGF bound to c-Met by anti-c-Met scFv. A, phage-displayed anti-c-Met scFv PC1, PC20 and PC21 were used to inhibit HGF binding to c-Met expressed on H1993 cells by ELISA. B, dose-dependent inhibition of HGF bound to c-Met protein by anti-c-Met scFv S1, S20 and S21 using competitive ELISA. C, schematic representation of domains of human c-Met protein. The Fc domain of human IgG1 was fused to carboxyl termini of c-Met$_{932}$ and c-Met$_{567}$. D, identification of epitopes of anti-c-Met scFvs using ELISA. E, determination of antagonized effect of anti-c-Met scFv with HGF in cancer cells.

To test whether the three anti-c-Met scFvs could inhibit HGF binding to c-Met, the human lung cancer cell line H1993 was chosen to undergo competition ELISA (Lutterbach B et al. (2007) *Cancer Res* 67:2081-2088). Control phage (Con-P) did not affect the binding under the same condition. HGF binding to H1993 cells without competitors was considered 100%. H1993 is known to express a high level of c-Met. When H1993 cells were incubated with HGF in the presence of the phage clones, the binding of HGF to H1993 cells was diminished by more than 90% by the anti-c-Met scFv PC1. PC20 inhibited more than 50% of HGF binding to c-Met (FIG. 2, panel A). The competitive inhibition of HGF by different concentrations of soluble scFvs was also tested. Normal mouse IgG (NMIgG) was used as a negative control. HGF binding to immobilized c-Met protein without competitors was considered 100%. As shown in FIG. 2, panel B, the binding activity of HGF to c-Met was dose-dependently inhibited by S1 and S20, but only slightly inhibited by S21. The IC$_{50}$ for HGF binding to c-Met was 27.4 nM and 249.5 nM for S1 and S20, respectively (FIG. 2, panel 8).

Therefore, binding epitopes of anti-c-Met scFvs localized within HGF binding domain of c-Met were investigated. The binding ability of anti-c-Met scFvs was examined for c-Met$_{932}$-Fc protein including whole extracellular domain of c-Met, and c-Met$_{567}$-Fc protein containing Sema and PSI domain, both of which have been defined as HGF binding regions (FIG. 2, panel C). The c-Met recombinant proteins were immobilized on titer wells, and incubated with anti-c-Met scFvs. Anti-c-Met polyclonal antibody and anti-E tag antibody was used as a positive and negative control, respectively. As shown in FIG. 2, panel D, S21 dramatically decreased its binding activity for c-Met$_{567}$-Fc compared to that for c-Met$_{932}$-Fc. The binding intensity of S1 for c-Met$_{932}$-Fc was similar to that for c-Met$_{567}$-Fc. S20 bound to c-Met$_{567}$-Fc less efficiently than that to c-Met$_{932}$-Fc. These results indicate that binding epitopes of S1 and S20 are located in HGF binding region of c-Met, whereas S21 recognizes c-Met through Ig-like domain (FIG. 2, panel D).

Since the anti-c-Met scFv S1 presented superiorly competitive capability, whether S1 would antagonize HGF to activate c-Met in cancer cells was examined. A549 cells were co-treated with HGF and S1 at 37° C. for 15 min. Total cell lysate was subjected to Western blotting using anti-tyrosine-phosphorylated c-Met antibody and an antibody against the c-Met β-chain (c-Met). Quantification of phosphorylated c-Met was based on luminescence intensity and normalized with total c-Met. HGF-induced c-Met phosphorylation was suppressed by S1, inhibiting 65.7% of c-Met phosphorylation relative to cancer cells without S1 treatment (FIG. 2, panel E).

Example 4

Examination of Anti-c-Met scFv Internalization Using Confocal Microscopy

Figure 3:
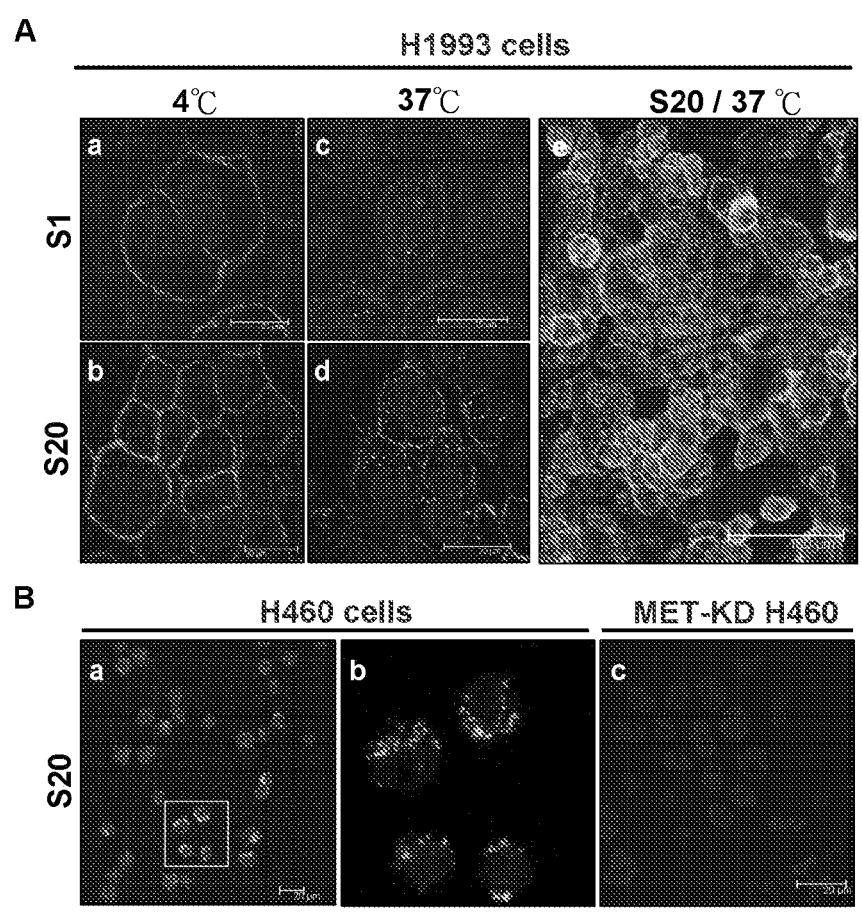
FIG. 3. Analysis of anti-c-Met scFv internalization using confocal microscopy. A, H1993 cells were separately incubated with anti-c-Met scFv S1 and S20 at 4° C. (a and b) or 37° C. for 30 min (c and d). Internalized S20 was observed in most of the cells under low-power magnification (e). The arrows indicate endocytosed scFv in cells. B, internalization of S20 into cells occurred through c-Met-mediated endocytosis. c-Met wildtype (a) and knockdown H460 cells (MET-KD) (c) were incubated with S20 at 37° C. for 30 min. The higher magnification field showed abundant S20 internalized to the cells (b).

The internalizing ability of an antibody is critical for the development of antibody-mediated liposomal drugs (Sapra and Allen (2002) *Cancer Res* 62:7190-7194). Internalization studies of anti-c-Met scFv S1 and S20 were performed at 37° C. in H1993 cells. The scFvs were detected with anti-E tag antibody followed by incubating with FITC-labeled secondary antibody after cells were fixed and permeabilized. Cell nuclei were stained with DAPI. Confocal microscopy showed that the scFvs bound to cell membranes at 4° C. (FIG. 3A, a and b), and internalizing scFv emitted fluorescent signals within cell cytoplasm at 37° C. (FIG. 3, panel A; c and d). The amount of fluorescent signaling in S20-treated H1993 cells was higher than S1-treated cells, suggesting the internalized ability of S20 was superior to that of S1. Under low-power magnification, internalizing S20 was observed in most of the cancer cells (FIG. 3, panel A; e).

Furthermore, to verify whether uptake of S20 was dependent on c-Met expression on the cell surface, internalization experiments were carried out in H460 and c-Met knockdown H460 cells. Confocal microscopy revealed S20 fluorescent signals within cytoplasm of H460 cells (FIG. 3, panel B; a and b), but not in c-Met knockdown H460 cells (FIG. 3, panel B; c). These results indicate that the anti-c-Met scFv S20 displayed specific internalization in c-Met-expressed cancer cells. As such, it can be used in the development of antibody-mediated intracellular drug delivery.

Example 5

Figure 11:
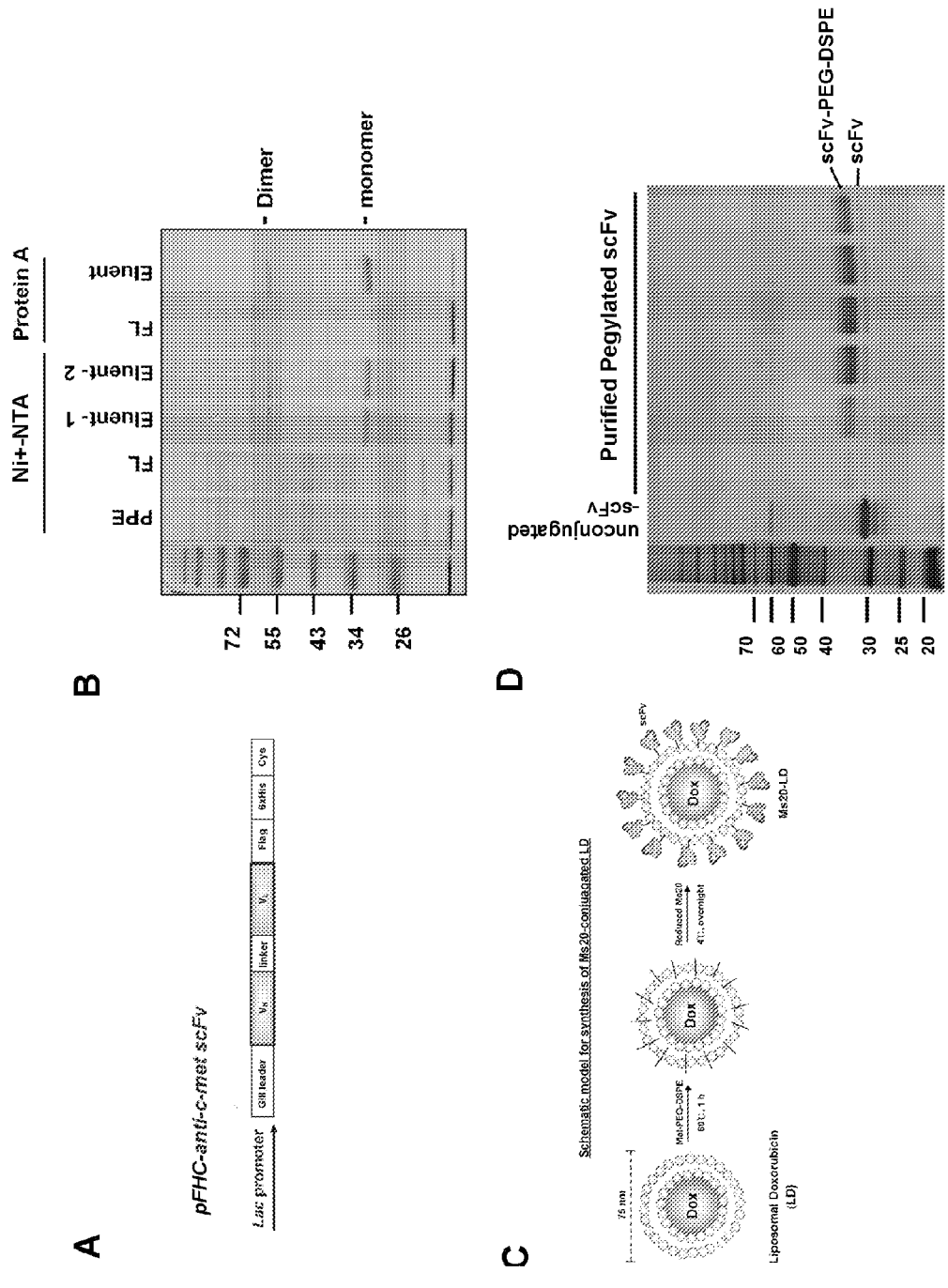
FIG. 11. Synthesis of Ms20-conjugated liposomal doxorubicin (Ms20-LD). A, schematic representation of construction of a prokaryotic vector pFHC-S20 to express the scFv protein containing a Flag tag, hexahistidine, and a cysteine residue at carboxyl terminus (Ms20). B, SDS-PAGE analysis and coomassie blue staining of purified Ms20 using Ni+ NTA sepharose and protein A agarose chromatography. PPE refers to periplasmic extract; FL refers to flow through. C, a schematic model shows conjugation procedures of the reduced Ms20 with maleimide-PEG-DSPE-incorporated LD. D, SDS-PAGE analysis and silver nitrate staining for Ms20-conjugated LD after purification by sepharose 4B gel filtration. Lane 3-8: Ms20 after conjugation to maleimide-PEG-DSPE (upper band).
Figure 12:
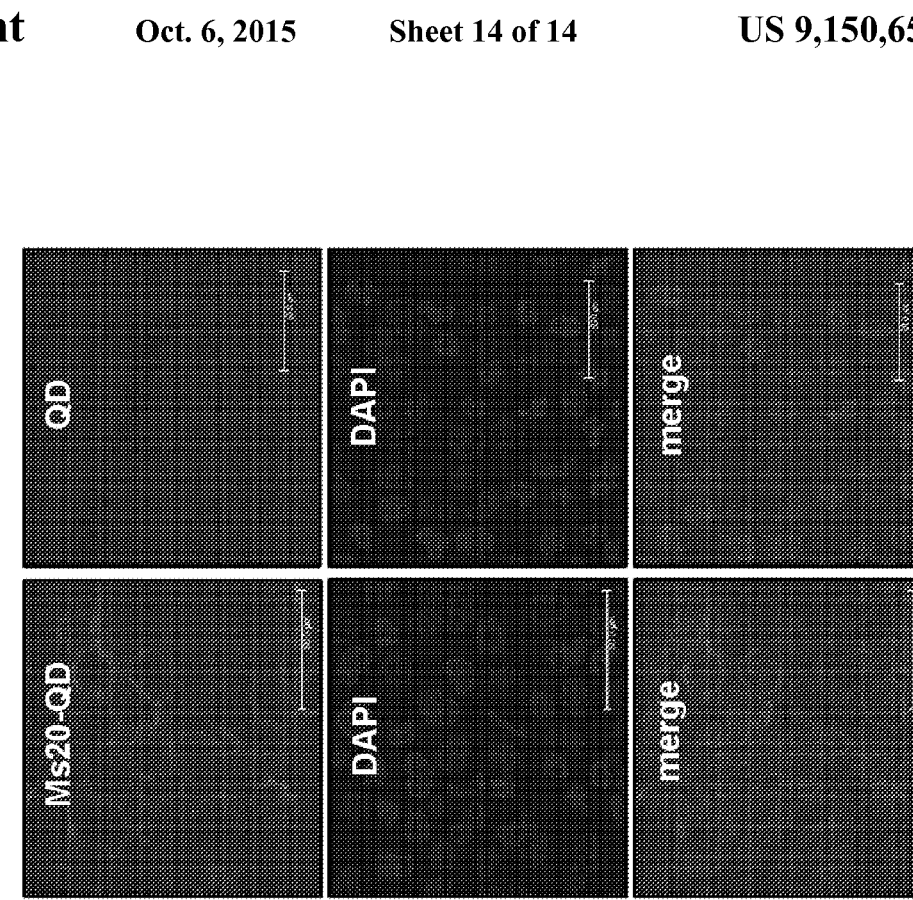
FIG. 12. Identification of c-Met expression on human lung cancer cell lines by FACS analysis using Ms20-QD. A, Human lung cancer cell lines were incubated with 10 µM Ms20-QD and QD at 4° C. for 1 hr. FACS analysis was performed to evaluate binding activity. B, H1993 cells was incubated with 50 nM Ms20-QD at 37° C. for 30 min. Binding and uptake of Ms20-QD by H1993 cells were examined using confocal microscopy. Scale bar, 50 µm.
Figure 12:
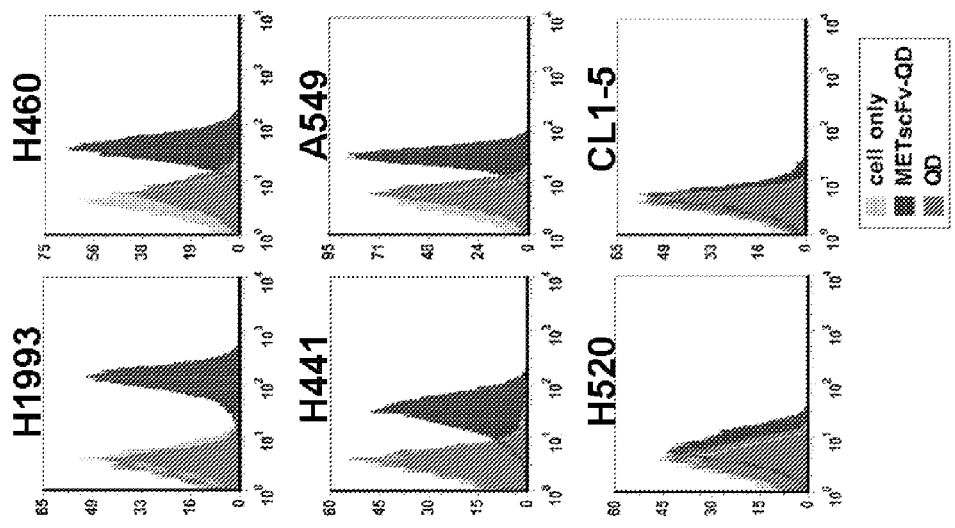

Ms20-Conjugated Nanoparticles Enhanced Drug Binding, Intracellular Delivery and Cytotoxicity To investigate whether S20 could promote liposomal drug delivery in c-Met-expressing tumor cells, a bacteria expression vector encoding S20 gene fused with a cysteine at C-terminal was created, and this S20-cysteine fusion protein was subsequently produced, which is referred to herein as Ms20 (FIG. 11, panels A and B). Site-directed conjugation Ms20 was specifically coupled through its c-terminal cysteine to maleimide-modified PEG chains on external surface of liposome containing doxorubicin, producing Ms20-conjugated liposomal doxorubicin (Ms20-LD) (FIG. 11, panels C and D).

Figure 4:
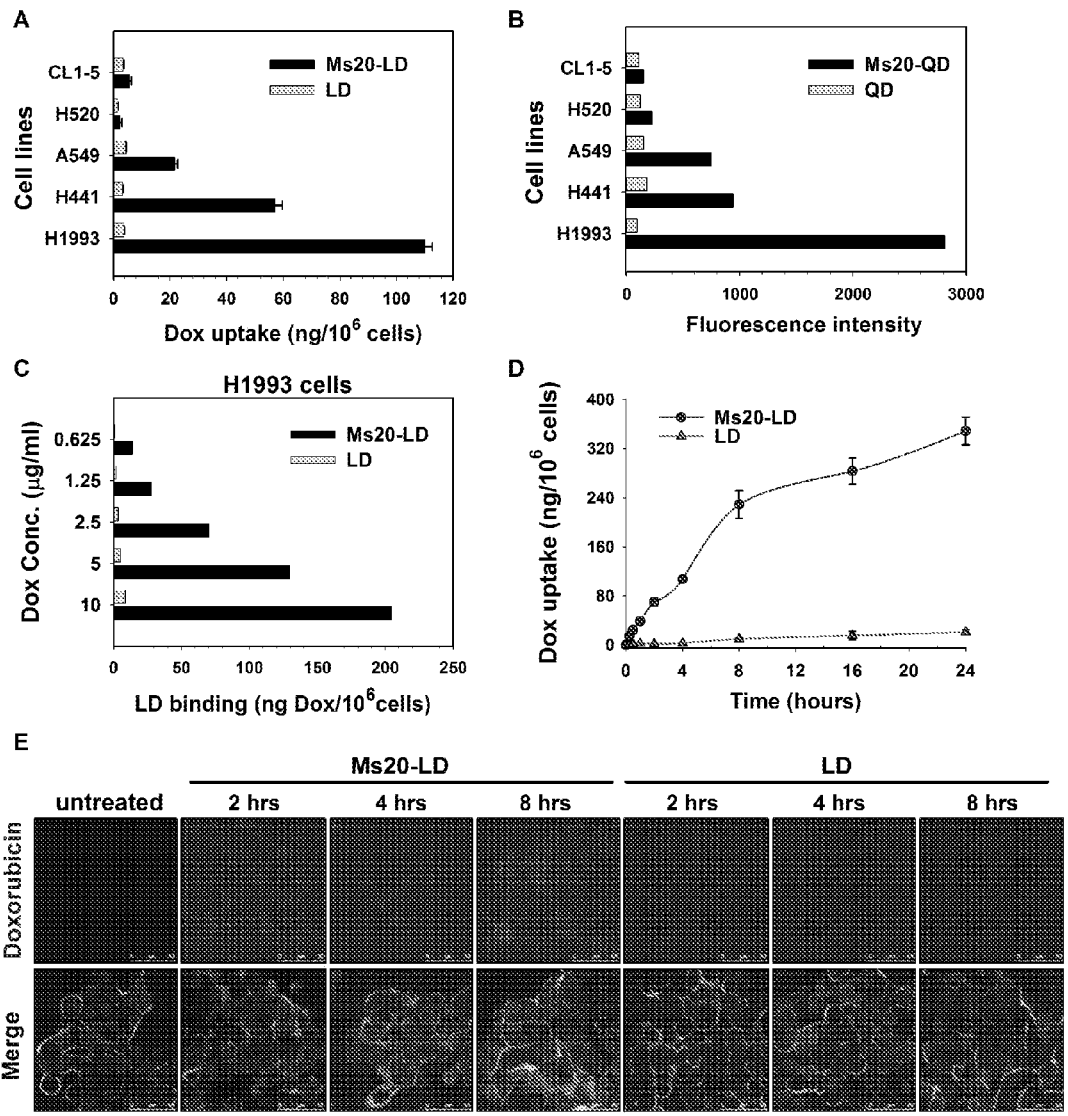
FIG. 4. Ms20 enhanced Liposomal Doxorubicin binding and internalization to human lung cancer cell lines. A, internalization studies of Ms20-LD and LD in lung cancer cell lines, which were incubated with drugs for 4 hr at 37° C. B, expression level of c-Met on cancer cell surface was determined by flow cytometry analysis using Ms20-QD. C, Binding of H1993 to liposomal drug. D, kinetics of liposomal drug uptake. E, uptake of Ms20-LD and LD by H1993 cells viewed with confocal microscopy after incubation at 37° C. for the indicated periods. Doxorubicin distributed in cytoplasm and nucleoplasm at 2 hrs incubation with Ms20-LD. After 8 hrs incubation with Ms20-LD, doxorubicin had predominantly accumulated within nucleus. Doxorubicin was very weakly detectable in the cells treated with LD. Lower panels show the images of doxorubicin signal (red) merged with cell membrane (green, pseudo-color) and nuclear (blue) staining. Scale bar, 50 μm.

To elucidate whether Ms20-conjugated liposome would increase drug delivery into cancer cells, several human lung cancer cell lines were treated with Ms20-LD and LD at 37° C. After acid glycine buffer wash, which removed surface-bound liposomal drugs, the internalized doxorubicin was quantified. Cellular uptake of doxorubicin was substantially elevated in H1993, H441 and A549 cells by treatment with Ms20-LD but there were no significant changes in H520 and CL1-5 cells (FIG. 4, panel A). To further verify the dependence of Ms20-LD uptake on cellular c-Met expression, the relative c-Met expressions on the respective cell lines were compared by flow cytometry using Ms20-labeled quantum dots (Ms20-QD) (FIG. 4, panel 8). Interestingly, H520 and CL1-5 cells were found to expressed only minimal amounts of c-Met (FIG. 4, panel 8), which corresponded to their poor uptake of Ms20-LD (FIG. 4, panel A). This finding suggests Ms20-LD uptake by tumor cells depended on c-Met expression level on the cell surface.

To verify that Ms20 was indeed capable of improving binding efficiency of LD on tumor cells, H1993 cells were separately incubated with varying concentrations of Ms20-LD and non-targeted LD (LD) at 4° C. for 1 hr. The binding activity of liposomal drug was quantified by fluorescence after lysing the cells. Compared to LD, Ms20-LD binding to H1993 cells was dramatically increased by 13- to 26-fold depending on drug concentration (FIG. 4, panel C). Similar results were observed for H460 cells under the same experimental conditions. To confirm that Ms20 enhanced intracellular drug delivery to cancer cells, H1993 cells were incubated with Ms20-LD and LD at elapsed time points. After surface stripping non-internalized liposomal drug, intracellular doxorubicin uptakes were measured. Ms20 markedly enhanced drug delivery to cancer cells compared with non-conjugated LD at each time point (FIG. 4, panel D).

Figure 5:
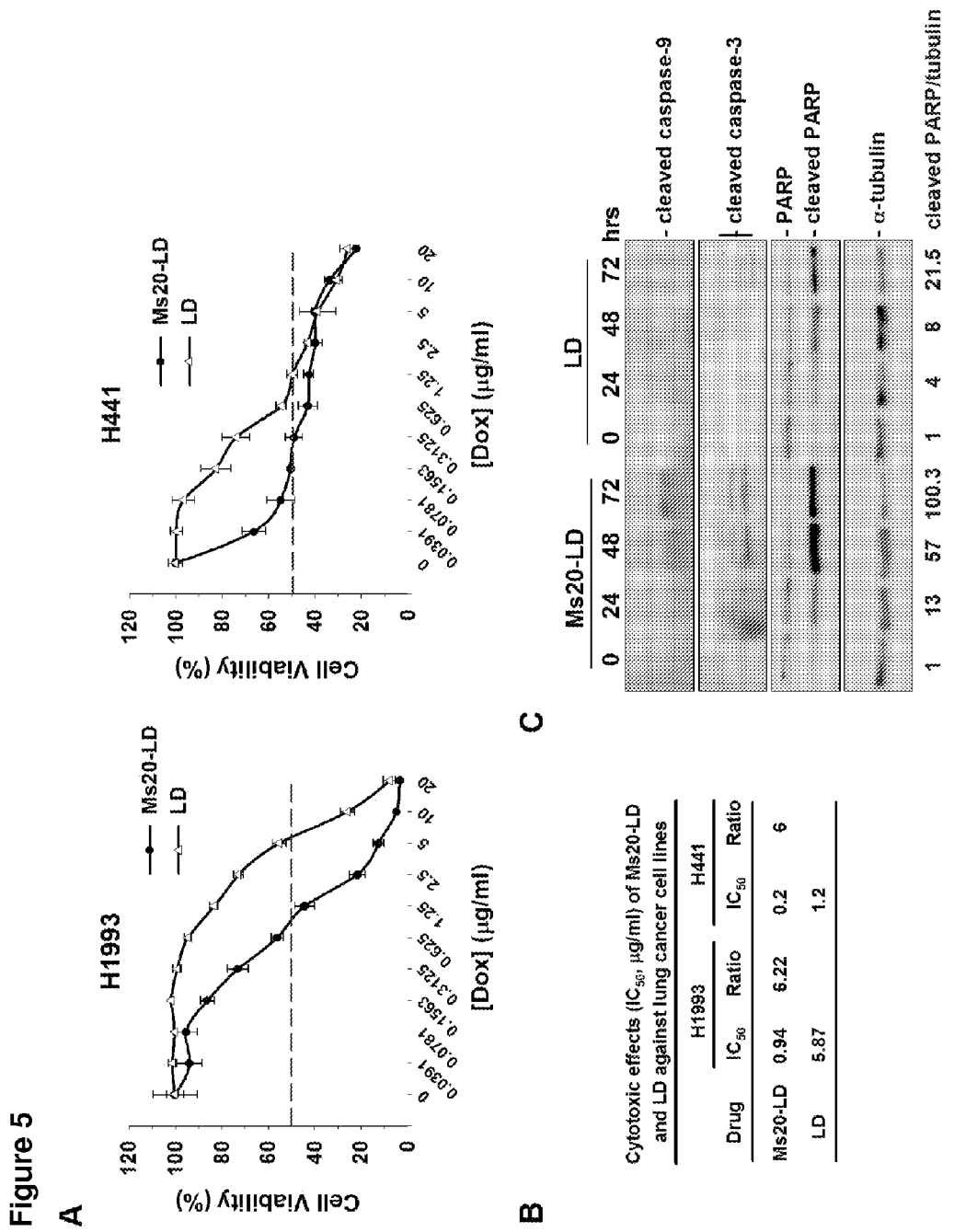
FIG. 5. Ms20-mediated liposomes enhanced doxorubicin-induced cytotoxic effect. A, in vitro cytotoxicity assay of human lung cancer cell lines treated with Ms20-LD and LD at varying concentrations. B, the IC$_{50}$ ratios were calculated to elucidate enhancement in cytotoxicity of Ms20-LD over LD. C, Western blot analysis of H1993 cells after treatment with 2.5 μg/ml of Ms20-LD and LD for 0, 24, 48 and 72 hours, respectively.

To further evaluate whether Ms20 could enhance the cytotoxicity of LD, the cytotoxic effect of Ms20-LD was studied on human lung cancer cells using MTT assay (FIG. 5, panel A). Cell viability was calculated as a percentage of living cells. Red dashed lines refer to mean 50% viability. Each point represents the mean of four experiments. Compared with LD, Ms20-LD significantly enhanced drug cytotoxicity to cancer cells, and decreased a half maximal inhibitory concentration (IC$_{50}$) by 6-fold in H1993 and H441 cells (FIG. 5, panel B). Expression of the apoptotic markers such as cleavage PARP, cleavage caspase 9 and cleavage caspase 3, were also enhanced by Ms20-LD-treated H1993 cells (FIG. 5, panel C). α-tubulin was probed as a loading control. Densitometry was used to estimate the fold increase of cleaved PARP compared with non-treated cells and normalized by α-tubulin (bottom).

Example 6

In Vivo Tumor Homing and Imaging of Anti-c-Met scFv

Figure 6:
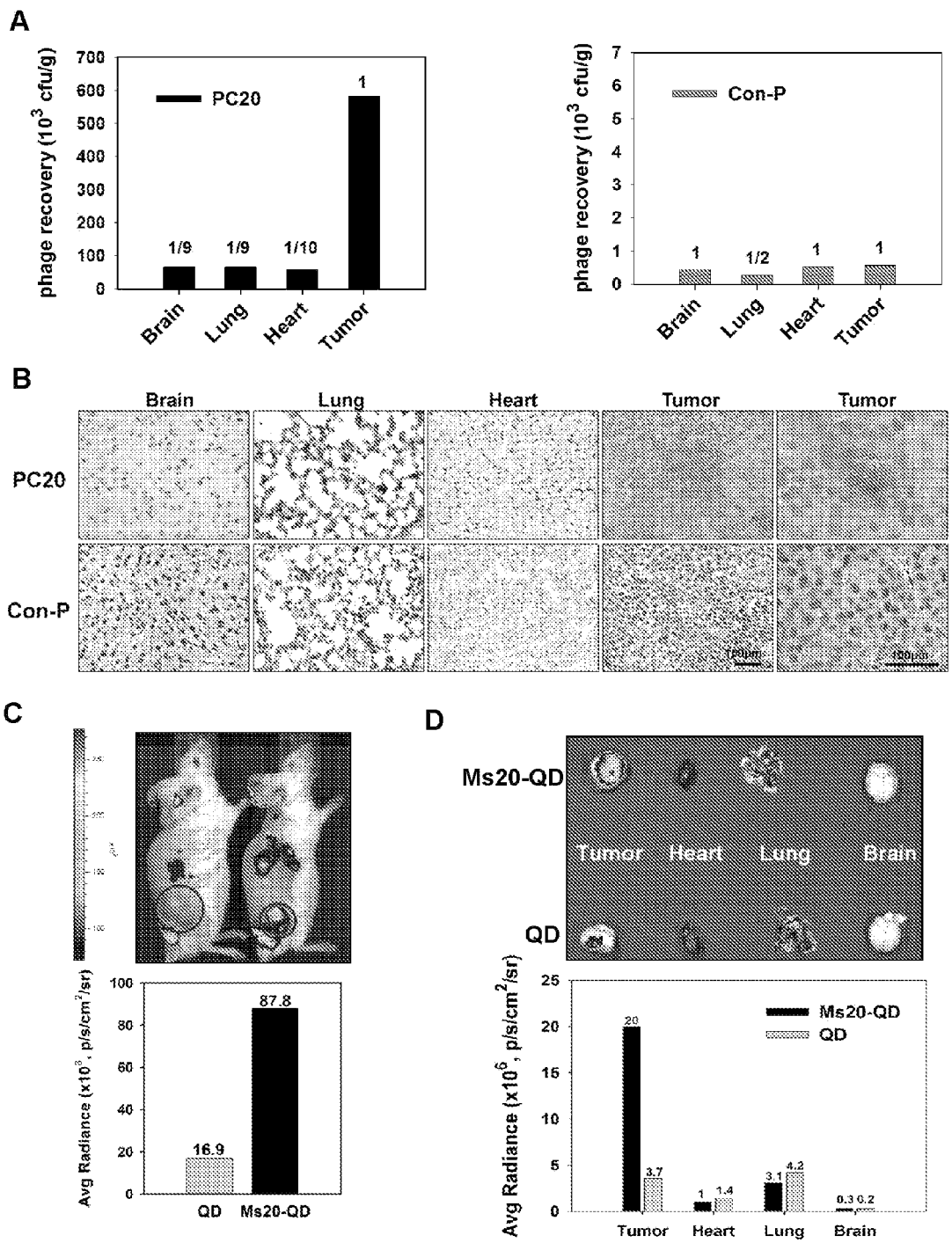
FIG. 6. Identification of tumor-homing ability of anti-c-Met scFv in human lung cancer xenograft. A, SCID mice bearing human lung cancer H460 xenografts were injected intravenously with PC20 and control phages (Con-P), respectively. B, examination of PC20 localization by immunohistochemical staining in homing assay. C, in vivo imaging of SCID mice bearing H1993 human lung tumor after intravenously injection of 400 pmole of Ms20-QD (quantum dots) (right) or QD (left). The NIR fluorescence images were acquired at post-injection with 6 hours (upper panel). Red circles indicate the tumor loci. The signal intensity of the tumor area was quantified by IVIS software (lower panel). D, the tissue distribution of Ms20-QD and QD were determined at 24 hr post-injection. The mice were sacrificed and the NIR images of the dissected organs were acquired (upper panel). The signal intensity of the tumor and the organs was measured by IVIS software (lower panel).

To investigate tumor homing ability of anti-c-Met scFv in vivo, the mice bearing H460-derived lung tumor xenografts were intravenously injected with anti-c-Met scFv PC20 or control phage. The titer of PC20 recovered from tumor was higher than that from visceral organs. The experiment was performed two times and obtained the same result. After perfusion, the binding phages were recovered and determined from tumor mass and normal organs. The results showed anti-c-Met scFv PC20 homed to the tumor far more efficiently than to normal organs (FIG. 6, panel A). Control phage had no such homing ability. Additionally, tissue distribution of anti-c-Met scFv PC20 was examined using anti-phage antibody to immunostain the tissue sections. PC20 phages were found to selectively localize in tumor tissues rather than in normal organ tissues such as brain, lungs, and heart, which were also derived from PC20-treated mice, whereas there was no control phage detected in tumor and normal organ tissues (FIG. 6, panel B).

To test whether anti-c-Met scFv S20 might be applied to tumor imaging assay, Ms20-conjugated quantum dots (Ms20-QD) or non-conjugated quantum dots (QD) were injected in mice bearing H1993-derived lung tumor xenografts. At 6 hours post-injection, the near-infrared (NIR) fluorescence signal intensity observed in tumor tissues of Ms20-QD-treated mouse was 5.2-fold higher than that of QD-treated mouse (FIG. 6, panel C). After 24 hours injection, the mice were sacrificed and anatomized to investigate tissue distribution of Ms20-QD. The representative image is the result of three independent experiments. As shown in FIG. 6, panel D, Ms20-QD strongly and selectively accumulated in the tumor as opposed to in the normal organs. Ms20-QD targeted to the tumor 5.4-fold more efficiently than QD. These results suggest that anti-c-Met scFv is suitable for uses in tumor imaging.

Example 7

Therapeutic Efficacy of Ms20-LD in Human Lung Carcinoma Xenografts

Figure 7:
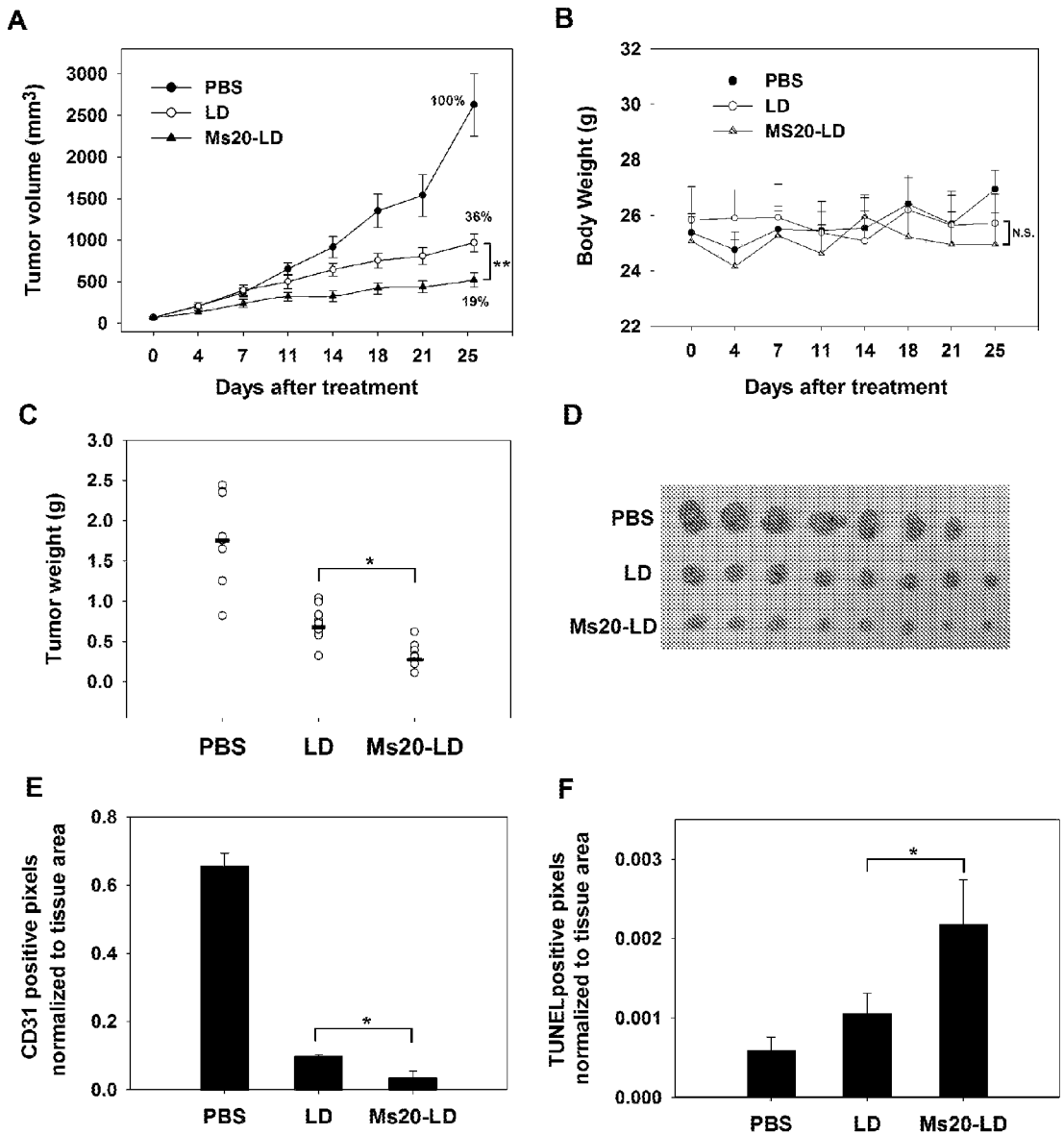
FIG. 7. Therapeutic efficacy of Ms20-LD in human lung cancer xenografts. A, Tumor volumes of mice bearing H460-derived lung cancer that were administered Ms20-LD, LD, or PBS. B, body weight of each group. C, tumor weight at the end of the treatment. D, Representative image of analysis depicted in C. E, investigation of tumor vessels in tumor tissue. F, analysis of apoptotic cells in tumor area using TUNEL assay. Error bar, SE. *, P<0.05.

To evaluate whether Ms20 could improve the chemotherapeutic efficacy of anticancer drug, a targeted drug delivery system was formulated by coupling Ms20 with PEGylated liposomal doxorubicin (Ms20-LD). SCID mice bearing H460 xenografts (~75 $mm^3$) were injected intravenously with liposomal drugs at a total doxorubicin dosage of 4 mg/kg (1 mg/kg at weekly intervals). Mice bearing H460-derived lung cancer were administered Ms20-LD, LD, and PBS. The tumor sizes of mice in the LD-group and in the control PBS group were 1.9- and 4.4-fold larger than that of the Ms20-LD group, respectively (n=8) , $P<0.01$. Points of the graph represent mean tumor volumes. The tumors in mice administrated Ms20-LD were found to be smaller in volume than those administer LD alone ($P<0.01$) (FIG. 7, panel A). The tumor size of the LD group was gradually increased to 1.9-fold that of the Ms20-LD by day 25. The Ms20-LD and LD groups did not have significant changes in body weight during treatment period (FIG. 7, panel B). By the end of the treatment, the final average tumor weight in mice treated with Ms20-LD was 0.31 g, compared to 0.73 g in mice treated with LD and 1.8 g in mice injected with PBS buffer (FIG. 7**, panels C and D). Thus, the tumor weight was lower in the Ms20-LD group than in the LD group (n=8) *, $P<0.05$. In addition, tumor tissues in each group were examined by anti-CD31 antibody to detect tumor blood vessels and terminal deoxynucleotidyl transferase dUTP nick end labeling (TUNEL) assay to identify apoptotic cells. The sections were analyzed using automated cell acquisition (TissueGnostics), and CD31-positive and TUNEL-positive area were quantified using MetaMorph software (Molecular Devices). As shown in FIG. 7, panel E, there was a greater decrease in CD31-positive areas in the Ms20-LD-treated group than in the LD-treated group. Thus, the amount of CD31 positive endothelium in Ms20-LD group was lower than in the LD group. The number of apoptotic cells in Ms20-LD-treated group was twice than that in LD-treated group (FIG. 7, panel F).

What is claimed is:

1. An isolated monoclonal antibody that binds to human c-Met, comprising:
   a heavy chain variable region wherein the variable region comprises as a CDR1 the sequence of SEQ ID NO:10; as a CDR2 the sequence of SEQ ID NO:12, and as a CDR3 the sequence of SEQ ID NO:22; and
   a light chain variable region wherein the variable region comprises as a CDR1 the sequence of SEQ ID NO:31, as a CDR2 the sequence of SEQ ID NO:33, and as a CDR3 the sequence of SEQ ID NO:43.

2. The isolated monoclonal antibody of claim 1, wherein said antibody comprises a) a full length VH of clone 1, comprising SEQ ID NO:9 joined to SEQ ID NO:10 joined to SEQ ID NO:11 joined to SEQ ID NO:12 joined to SEQ ID NO:21 joined to SEQ ID NO:22 joined to SEQ ID NO:23; and b) a full length VL of clone 1 comprising SEQ ID NO:30 joined to SEQ ID NO:31 joined to SEQ ID NO:32 joined to SEQ ID NO:33 joined to SEQ ID NO:42 joined to SEQ ID NO:43 joined to SEQ ID NO:44.

3. An isolated monoclonal antibody that binds to human c-Met comprising:
   a heavy chain variable region wherein the variable region comprises as a CDR1 the sequence of SEQ ID NO:14; as a CDR2 the sequence of SEQ ID NO:16, and as a CDR3 the sequence of SEQ ID NO:25; and
   a light chain variable region wherein the variable region comprises as a CDR1 the sequence of SEQ ID NO:35; as a CDR2 the sequence of SEQ ID NO:37, and as a CDR3 the sequence of SEQ ID NO:46.

4. The isolated monoclonal antibody of claim 3, wherein said antibody comprises a) a full length VH of clone 20 comprising SEQ ID NO:13 joined to SEQ ID NO:14 joined to SEQ ID NO:15 joined to SEQ ID NO:16 joined to SEQ ID NO:24 joined to SEQ ID NO:25 joined to SEQ ID NO:26; and b) a full length VL of clone 20 comprising SEQ ID NO:34 joined to SEQ ID NO:35 joined to SEQ ID NO:36 joined to SEQ ID NO:37 joined to SEQ ID NO:45 joined to SEQ ID NO:46 joined to SEQ ID NO:47.

5. The isolated monoclonal antibody of claim 3 that, when bound to c-Met on the surface of a living mammalian cell, is endocytosed by the cell.

6. The isolated monoclonal antibody of claim 3, wherein said anybody is a single chain Fv (scFv), IgG, Fab, (Fab')2, or (scFv')2.

7. The isolated monoclonal antibody of claim 3, wherein said antibody is labeled.

8. The isolated monoclonal antibody of claim 3, wherein said antibody is conjugated to an anti-cancer agent.

9. A lipidic nanoparticle comprising a surface and an interior space, said interior space comprising an anti-cancer agent, wherein an isolated monoclonal antibody of claim 3 is attached to the surface of said lipidic nanoparticle.

10. The lipidic nanoparticle of claim 9, wherein when the lipidic nanoparticle is contacted with a cell expressing cell surface c-Met, said antibody binds to the cell surface c-Met and the lipidic nanoparticle is endocytosed.

11. A composition comprising:
    a pharmaceutically acceptable carrier; and
    an isolated monoclonal antibody of claim 3.

12. The composition of claim 11, wherein said composition is formulated for parenteral administration.

13. The composition of claim 11, wherein said composition is formulated for intravenous, intrathecal, or intraventricular administration.

14. A kit comprising a composition of claim 11.

15. An isolated monoclonal antibody that binds to human c-Met comprising:
    a heavy chain variable region wherein the variable region comprises as a CDR1 the sequence of SEQ ID NO:18; as a CDR2 the sequence of SEQ ID NO:20, and as a CDR3 the sequence of SEQ ID NO:28;

and a light chain variable region wherein the variable region comprises as a CDR1 the sequence of SEQ ID NO:39; as a CDR2 the sequence of SEQ ID NO:41, and as a CDR3 the sequence of SEQ ID NO:49.

16. The isolated monoclonal antibody of claim 15, wherein said antibody comprises: a) a full length VH of clone 21 comprising SEQ ID NO:17 joined to SEQ ID NO:18 joined to SEQ ID NO:19 joined to SEQ ID NO:20 joined to SEQ ID NO:27 joined to SEQ ID NO:28 joined to SEQ ID NO:29; and b) a full length VL of clone 21 comprising SEQ ID NO:38 joined to SEQ ID NO:39 joined to SEQ ID NO:40 joined to SEQ ID NO:41 joined to SEQ ID NO:48 joined to SEQ ID NO:49 joined to SEQ ID NO:50.

* * * * *